United States Patent
Kulangara et al.

(10) Patent No.: US 11,585,817 B2
(45) Date of Patent: *Feb. 21, 2023

(54) SCORING METHODS FOR ANTI-PD THERAPY ELIGIBILITY AND COMPOSITIONS FOR PERFORMING SAME

(71) Applicants: Agilent Technologies, Inc., Santa Clara, CA (US); Merck Sharp & Dohme Corp., Rahway, NJ (US)

(72) Inventors: Karina Kulangara, Carpinteria, CA (US); Nancy Zhang, Thousand Oaks, CA (US); David Stanforth, Carpinteria, CA (US); Greg Angelides, Philadelphia, PA (US); Stephanie Waldroup, Santa Barbara, CA (US); Kenneth Emancipator, Bernardsville, NJ (US)

(73) Assignees: AGILENT TECHNOLOGIES, INC., Santa Clara, CA (US); MERCK SHARP & DOHME LLC, Rahway, NJ (US)

( * ) Notice: Subject to any disclaimer, the term of this patent is extended or adjusted under 35 U.S.C. 154(b) by 263 days.

This patent is subject to a terminal disclaimer.

(21) Appl. No.: 16/804,395

(22) Filed: Feb. 28, 2020

(65) Prior Publication Data

US 2020/0200759 A1 Jun. 25, 2020

Related U.S. Application Data

(63) Continuation of application No. 15/422,350, filed on Feb. 1, 2017, now Pat. No. 10,613,092.

(60) Provisional application No. 62/317,179, filed on Apr. 1, 2016.

(51) Int. Cl.
G01N 33/574 (2006.01)

(52) U.S. Cl.
CPC .......... *G01N 33/57492* (2013.01); *G01N 2333/70532* (2013.01); *G01N 2800/52* (2013.01)

(58) Field of Classification Search
CPC ... G01N 33/57492; G01N 2333/70532; G01N 2800/52
USPC ........................................................ 435/7.23
See application file for complete search history.

(56) References Cited

U.S. PATENT DOCUMENTS

| | | | |
|---|---|---|---|
| 10,613,092 B2 * | 4/2020 | Kulangara | ....... G01N 33/57492 |
| 2016/0009805 A1† | 1/2016 | Kowanetz et al. | |
| 2016/0084839 A1† | 3/2016 | Dolled-Filhart et al. | |
| 2016/0222118 A1 | 8/2016 | Chen et al. | |

FOREIGN PATENT DOCUMENTS

| WO | 2014/151006 A2 † | 9/2014 |
|---|---|---|
| WO | 2015/181343 A2 † | 12/2015 |

OTHER PUBLICATIONS

Kim, et al., "PD-L1 expression on immune cells, but not on tumor cells, is a favorable prognostic factor for head and neck cancer patients", Scientific Reports, 2016, 6: 36956.
Lyford-Pike, et al., "Evidence for a role of the PD-1:PD-L1 pathway in immune resistance of HPV-associated head and neck squamous cell carcinoma", Cancer Res., 2013, 73(6): 1733-1741.
Straub, et al., "CD274/PD-L1 gene amplification and PD-L1 protein expression are common events in squamous cell carcinoma of the oral cavity", Oncotarget, 2016, 7(11): 12024-12034.
Carbognin et al., Differential Activity of Nivolumab, Pembrolizumab and MPDL3280A according to the Tumor Expression of Programmed Death Ligand 1 PD L1 Sensitivity Analysis of Trials in Melanoma, Lung and Genitourinary Cancers.†
Garon et al., Pembrolizumab for the Treatment of Non Small Cell Lung Cancer.†
Phillips et al., Development of an Automated PD L1 Immunohistochemistry IHC Assay for Non Small Cell Lung Cancer.†
Choueiri et al., PD L1 expression in nonclear-cell renal cell carcinoma.†
Muro, Clinical outcomes in patients with advanced gastric cancer treated with pembrolizumab MK 3475 in Keynote 012.†
Label for Dako, PD L1 IHC 22C3 pharmDx.†

* cited by examiner
† cited by third party

*Primary Examiner* — Yan Xiao

(57) ABSTRACT

Aspects of the present disclosure provide methods for determining the eligibility of a subject having a malignancy for treatment with an anti-PD therapeutic agent based on a Combined Positive Score (CPS) for a tumor tissue sample from the subject. Compositions and kits or performing the disclosed methods are also provided.

22 Claims, 10 Drawing Sheets
(9 of 10 Drawing Sheet(s) Filed in Color)

SCORING METHODS FOR ANTI-PD THERAPY ELIGIBILITY AND COMPOSITIONS FOR PERFORMING SAME

CROSS-REFERENCING

This application is a continuation application of U.S. patent application Ser. No. 15/422,350 filed on Feb. 1, 2017 which claims the benefit of provisional application Ser. No. 62/317,179, filed on Apr. 1, 2016, the disclosure of both applications is incorporated by reference herein in its entirety.

BACKGROUND

Programmed cell death 1 ligand 1 (PD-L1) expression is implicated in evasion of immune responses involved in many contexts, including suppression of anti-tumor immune activity. PD-L1 expression has been shown in situ on a wide variety of solid tumors including breast, lung, colon, ovarian, melanoma, bladder, liver, salivary, stomach, gliomas, thyroid, thymic epithelial, and head and neck cancers (Brown J A et al., 2003. J. Immunol. 170:1257-66; Dong H et al. 2002. Nat. Med. 8:793-800; Hamanishi J, et al. 2007. Proc. Natl. Acad. Sci. USA 104:3360-65; Strome S E et al. 2003. Cancer Res. 63:6501-5; Inman B A et al. 2007. Cancer 109:1499-505; Konishi Jet. al. 2004. Clin. Cancer Res. 10:5094-100; Nakanishi Jet. al. 2007. Cancer Immunol. Immunother. 56:1173-82; Nomi T et al. 2007. Clin. Cancer Res. 13:2151-57; Thompson R H et al. 2004. Proc. Natl. Acad. Sci. USA 101:17174-79; Wu C, Zhu Y, Jiang J, Zhao J, Zhang X G, Xu N. 2006. Acta Histochem. 108:19-24). In addition, PD-1 expression can be upregulated on tumor infiltrating lymphocytes (TILs), and this may also contribute to tumor immunosuppression (Blank C et al. 2003. J. Immunol. 171:4574-81).

In ovarian cancer, PD-L1 expression is inversely correlated with intraepithelial, but not stromal, infiltrating CD8 T cells, suggesting that PD-L1 inhibits the intratumor migration of CD8 T cells (Hamanishi J et. al. 2007. Proc. Natl. Acad. Sci. USA 104:3360-65). Translation of PD-L1 mRNA is enhanced by loss of PTEN and the ensuing activation of Akt, a common event in tumorigenesis (Parsa A T et al. 2007. Nat. Med. 13:84-88). Studies relating PD-L1 expression on tumors to disease outcome show that PD-L1 expression strongly correlates with unfavorable prognosis in kidney, ovarian, bladder, breast, gastric, and pancreatic cancer (Hamanishi J et al. 2007. Proc. Natl. Acad. Sci. USA 104:3360-65; Inman B A et al. 2007. Cancer 109:1499-505; Konishi J et. al. 2004. Clin. Cancer Res. 10:5094-100; Nakanishi J et. al. 2007. Cancer Immunol. Immunother. 56:1173-82; Nomi T et al. 2007. Clin. Cancer Res. 13:2151-57; Thompson R H et al. 2004. Proc. Natl. Acad. Sci. USA 101:17174-79; Wu C, Zhu Y, Jiang J, Zhao J, Zhang X G, Xu N. 2006. Acta Histochem. 108:19-24). In addition, these studies suggest that higher levels of PD-L1 expression on tumors may facilitate advancement of tumor stage and invasion into deeper tissue structures. Studies in animal models demonstrate that PD-L1 on tumors inhibits T cell activation and lysis of tumor cells and in some cases leads to increased tumor-specific T cell death (Dong H et al. 2002. Nat. Med. 8:793-800; Hirano F et al. 2005. Cancer Res. 65:1089-96).

Non-malignant cells have also been implicated in playing important roles in tumor maintenance and growth. For example, tumor-associated APCs can utilize the PD-1:PD-L pathway to control antitumor T cell responses (Curiel et al. 2003. Nat. Med. 9:562-67). In this study, PD-L1 expression on a population of tumor-associated myeloid DCs was shown to be up-regulated by tumor environmental factors.

Given the role PD-1/PD-L1 plays in tumor biology, therapeutic agents that target this molecule have been of significant interest. Indeed, anti-PD-1/PD-L1 therapy (or anti-PD therapy) has generated significant clinical benefits by inducing regression of advanced and metastatic tumors and improving survival. Anti-PD therapy can have durable effects, tolerable toxicity, and is applicable to a broad spectrum of cancer types, especially in solid tumors.

Examples of anti-PD therapeutics currently in use or in development include the following:

Nivolumab, Bristol-Myers Squibb (also known as Opdivo, MDX-1106, BMS-936558, and ONO-4538), was the first mAb targeting PD-1 to show significant clinical activity in unresectable or metastatic melanomas, non-small-cell lung carcinoma (NSCLC), and metastatic renal cell carcinomas.

Pembrolizumab, Merck (also known as Keytruda, lambrolizumab, and MK-3475), is an Anti-PD-1 monoclonal antibody that has shown similar efficacy and safety compared with nivolumab in a phase I clinical trial in advanced melanoma (NCT01295827) and is now an FDA-approved second-line drug for the treatment of melanoma. Pembrolizumab is also effective in patients with advanced NSCLC and has shown promising effects in other solid tumors, including advanced gastric cancer, advanced bladder cancer, head and neck cancer, classical Hodgkin's lymphoma, and triple-negative breast cancer.

BMS-936559, Bristol-Myers Squibb (also known as MDX-1105) is a fully human IgG4 anti-PD-L1 mAb that inhibits the binding of the PD-L1 ligand to both PD-1 and CD80 and has demonstrated therapeutic efficacy in a phase I clinical trial (NCT00729664).

MPDL3280A, Genentech/Roche, is an engineered anti-PD-L1 IgG1 mAb that can inhibit PD-L1 interactions with both PD-1 and B7-1. A study of metastatic urothelial bladder cancer (UBC) demonstrated that MPDL3280A has marked activity in controlling tumor growth. Moreover, owing to the mild side effects, including a lack of renal toxicity, patients with UBC, who are often older and have a higher incidence of renal impairment, are thought to tolerate MPDL3280A better than chemotherapy (NCT01375842). In an expansion phase I trial across multiple cancer types, including NSCLC, melanoma, renal cell carcinoma, and other tumors, responses to MPDL3280A were observed in patients with tumors expressing high levels of PD-L1, especially when PD-L1 was expressed by tumor infiltrating lymphocytes TILs.

Pidilizumab (Medivation/CureTech), MEDI4736 (AstraZeneca), and Avelumab (MSB0010718C; Merck-Sorono) are additional PD-L1 targeting antibody-based therapeutic agents that show promise in the treatment of multiple human cancers.

In addition to developing anti-PD therapeutic agents, work in this area has included performing more detailed analysis of not only the malignant cells in tumor biopsies, but also non-malignant cells to identify patients who may respond to these therapies. For example, some published scoring methods for PD-L1 immunohistochemistry (IHC) staining are either capturing percentage of staining and or staining intensity on tumor cells or the PD-L1 staining and staining intensity on tumor-associated immune cells (Phillips et al. Appl Immunohistochem Mol Morphol. 2015 September; 23(8): 541-549) (Garon et al. N Engl J Med. 2015 May 21; 372(21):2018-28. doi: 10.1056/NEJ- Moa1501824. Epub 2015 Apr. 19). More and more clinical trials indicated that in some tumor indications PD-L1 staining on both tumor and tumor-associated immune cells is associated with clinical outcome (Rosenberg et al., The Lancet, DOI: dx.doi.org/10.1016/S0140-6736(16)00561-4; Allred D, et al. *Mod Pathol.* 1998; 11:155-168).

While progress has been made in this area, it is clear that using current scoring methods to capture PD-L1 expression on tumor as well as non-tumor cells (e.g., immune cells) is not practical from an assay development standpoint, as it can double the pathologist's workload and/or lead to confusion with respect to having 2 different cutoffs (one for tumor cells and one for non-tumor cells). There is thus still a need to improve tumor tissue scoring methods for identifying patients that will respond effectively to anti-PD therapy.

SUMMARY

Aspects of the present disclosure provide methods for determining the eligibility of a subject having a malignancy for treatment with an anti-PD therapeutic agent based on a Combined Positive Score (CPS) for a tumor tissue sample from the subject. In certain embodiments, the method includes: determining the number of viable PD-L1 positive tumor cells, the number of viable PD-L1 negative tumor cells, and the number of viable PD-L1 positive mononuclear inflammatory cells (MIC) in a tumor tissue sample from a subject having a malignancy; and calculating a combined positive score (CPS) for the tumor tissue sample using the formula:

$$CPS = \frac{PD\text{-}L1 \text{ positive tumor cells} + PD\text{-}L1 \text{ positive } MIC}{PD\text{-}L1 \text{ positive tumor cells} + PD\text{-}L1 \text{ negative tumor cells}} \times 100\%$$

wherein the subject is eligible for treatment with an anti-PD therapeutic agent when the CPS is above a threshold. Compositions and kits for performing the methods are also provided.

BRIEF DESCRIPTION OF THE FIGURES

The patent or application file contains at least one drawing executed in color. Copies of this patent or patent application publication with color drawing(s) will be provided by the U.S. Patent and Trademark Office upon request and payment of the necessary fee.

Certain aspects of the following detailed description are best understood when read in conjunction with the accompanying drawings. It is emphasized that, according to common practice, the various features of the drawings are not to scale. On the contrary, the dimensions of the various features are arbitrarily expanded or reduced for clarity. Included in the drawings are the following figures.

DEFINITIONS

Figure 1:
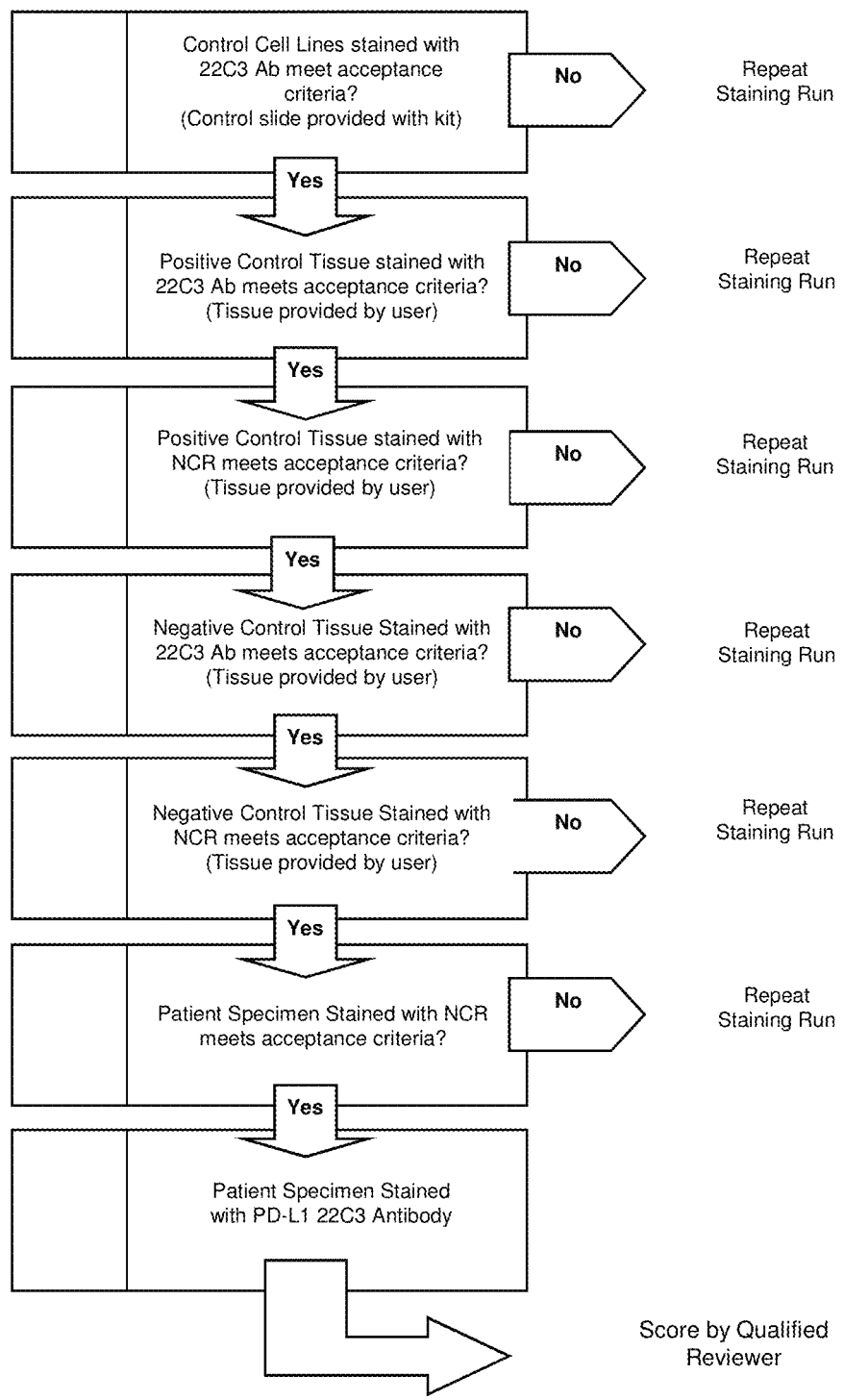
FIG. 1 provides an example of rules for evaluating control samples.

Unless defined otherwise herein, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

All patents and publications, including all sequences disclosed within such patents and publications, referred to herein are expressly incorporated by reference.

Numeric ranges are inclusive of the numbers defining the range. Unless otherwise indicated, nucleic acids are written left to right in 5' to 3' orientation; amino acid sequences are written left to right in amino to carboxy orientation, respectively.

The headings provided herein are not limitations of the various aspects or embodiments of the invention. Accordingly, the terms defined immediately below are more fully defined by reference to the specification as a whole.

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with the general meaning of many of the terms used herein. Still, certain terms are defined below for the sake of clarity and ease of reference.

The term "PD-L1" refers to the Programmed cell death ligand 1 molecule. PD-L1 may refer to human PD-L1 or homologs in other organisms, depending on the context in which it is used. Human PD-L1 is also known as CD274, B7-H, B7H1, B7-H1, B7 homolog 1, MGC142294, MGC142296, PDCD1L1, PDCD1LG1, PDCD1 ligand 1, PDL1, Programmed cell death 1 ligand 1 and Programmed death ligand 1 and has Uniprot number Q9NZQ7 and NCBI gene ID number 29126. Human PD-L1 is a 290 amino acid type I transmembrane protein encoded by the CD274 gene on human chromosome 9. Mouse PD-L1 has NCBI GenBank ID number ADK70950.1.

A "diagnostic marker" is a specific biochemical in the body which has a particular molecular feature that makes it useful for detecting a disease, measuring the progress of disease or the effects of treatment, or for measuring a process of interest.

The term "epitope" as used herein is defined as small chemical groups on the antigen molecule that is bound to by an antibody. An antigen can have one or more epitopes. In many cases, an epitope is roughly five amino acids or sugars in size. One skilled in the art understands that generally the overall three-dimensional structure or the specific linear sequence of the molecule can be the main criterion of antigenic specificity.

A "subject" of diagnosis or treatment is a plant or animal, including a human. Non-human animals subject to diagnosis or treatment include, for example, livestock and pets.

As used herein, the term "tissue section" refers to a piece of tissue that has been obtained from a subject and mounted on a planar surface, e.g., a microscope slide. The sample may be fixed and/or sectioned as desired. A "tumor tissue sample" or "tumor tissue biopsy sample" includes cells derived from a tumor in a subject, e.g., a human subject having a malignancy. Such tissue samples are sometimes referred to simply as a "biopsy".

A "cell suspension" is used to refer to any cellular sample in which single cells or very small cell aggregates are suspended in a liquid medium. Cell suspensions are used, e.g., in flow cytometry and other single-cell analysis methods. Cell suspensions can be obtained by processing a solid tissue sample from a subject, e.g., by treating the sample with enzymes, chemicals, and/or placing them under physically disruptive conditions that disaggregate the cells. Such methods are known in the art.

As used herein, the term "formalin-fixed paraffin embedded (FFPE) tissue section" refers to a piece of tissue, e.g., a biopsy that has been obtained from a subject, fixed in formaldehyde (e.g., 3%-5% formaldehyde in phosphate buffered saline) or Bouin solution, embedded in wax, cut into thin sections, and then mounted on a planar surface, e.g., a microscope slide.

As used herein, the term "resin embedded tissue section" refers to a piece of tissue, e.g. a biopsy that has been obtained from a subject, fixed, (e.g., in 3-5% glutaraldehyde in 0.1M phosphate buffer), dehydrated, infiltrated with epoxy or methacrylate resin, cured, cut into thin sections, and then mounted on a planar surface, e.g., a microscope slide.

As used herein, the term "cryosection" refers to a piece of tissue, e.g. a biopsy that has been obtained from a subject, snap frozen, embedded in optimal cutting temperature embedding material, frozen, cut into thin sections and fixed (e.g. in methanol or paraformaldehyde) and mounted on a planar surface, e.g., a microscope slide.

The term "staining" includes binding a target (e.g., an antigen) in a cellular sample with a target-specific binding agent (e.g., an antibody or a nucleic acid) and then detecting the presence of the target-specific binding agent on the cells of the cellular sample using a detectable label or chromogen. The detectable label can be directly conjugated to the target-specific binding agent (e.g., a primary antibody) or may be conjugated to a secondary reagent that binds specifically to an unlabeled target-specific reagent (e.g., a secondary antibody). In some cases, the target-specific reagent is itself detectable, and thus no additional attached label is needed.

By "fluorophore" or "fluorescent label" is meant any label that absorbs light at a first wavelength (or range of wavelengths) and emits light at a second, different wavelength (or range of wavelengths). In general, the emitted light from a fluorescent labels has a longer wavelength, and therefore lower energy, than the absorbed wavelength. Examples of fluorescent labels include, but are not limited to, phycobiliproteins (e.g., phycoerythrin (PE), phycocyanin (PC), allophycocyanin (APC)), rhodamine, fluorescein, alexa fluor, cascade blue, tetramethylrhodamine, Texas red, and the like, as well as those listed in greater detail below.

A "chromogen" or "chromogenic compound" and the like is a substance that can be converted into a colored compound under specific conditions, e.g., when acted upon by an enzyme or under specific chemical/reaction conditions. Examples of enzyme-substrate combinations include: (i) Horseradish peroxidase (HRP) with hydrogen peroxidase as a substrate, where the hydrogen peroxidase oxidizes a dye precursor [e.g., orthophenylene diamine (OPD) or 3,3',5,5'-tetramethyl benzidine hydrochloride (TMB)]; (ii) alkaline phosphatase (AP) with para-Nitrophenyl phosphate as chromogenic substrate; and (iii) β-D-galactosidase (β-D-Gal) with a chromogenic substrate (e.g., p-nitrophenyl-β-D-galactosidase) or fluorogenic substrate (e.g., 4-methylumbelliferyl-β-D-galactosidase). Numerous other enzyme-substrate combinations are available to those skilled in the art. For a general review of these, see U.S. Pat. Nos. 4,275,149 and 4,318,980.

As used herein, the term "target-specific binding agent" means any agent that specifically binds to a target or analyte of interest, e.g., a target of interest that is present in a tissue section as described herein (e.g., a polypeptide or polynucleotide). Examples of target-specific binding agents include antibodies, receptors, and ligands, or target-binding fragments thereof, polynucleotide probes, and the like.

As used herein, the term "multiplexing" refers to using more than one label, stain, and/or chromogen for the simultaneous or sequential detection and measurement of a target in a sample, e.g., a tissue section.

As used herein, the terms "antibody" and "immunoglobulin" are used interchangeably and are well understood by those in the field. Those terms refer to a protein consisting of one or more polypeptides that specifically binds an antigen. One form of antibody constitutes the basic structural unit of an antibody. This form is a tetramer and consists of two identical pairs of antibody chains, each pair having one light and one heavy chain. In each pair, the light and heavy chain variable regions are together responsible for binding to an antigen, and the constant regions are responsible for the antibody effector functions. These terms also include fragments of antibodies which retain specific binding to antigen or target, including, but not limited to, Fab, Fv, scFv, and Fd fragments, chimeric antibodies, humanized antibodies, single-chain antibodies, bi-specific hybrid antibodies, and fusion proteins comprising an antigen-binding portion of an antibody and a non-antibody protein. See, e.g., Hood et al., "Immunology", Benjamin, N.Y., 2nd ed. (1984); Hunkapiller and Hood, Nature, 323, 15-16 (1986); Lanzavecchia et al., Eur. J. Immunol. 17, 105-111 (1987); Huston et al., Proc. Natl. Acad. Sci. U.S.A., 85, 5879-5883 (1988); and Bird et al., Science, 242, 423-426 (1988) which are hereby incorporated by reference herein in their entirety.

As used herein, the terms "primary antibody" and "secondary antibody" refer to different antibodies, where a primary antibody is a polyclonal or monoclonal antibody from one species (rabbit, mouse, goat, donkey, etc.) that specifically recognizes an antigen (e.g., a biomarker) in a sample (e.g., a human tissue sample) under study, and a secondary antibody is an antibody (usually polyclonal) from a different species that specifically recognizes the primary antibody, e.g., in its Fc region.

Sometimes, the label may be indirectly conjugated with the antibody. The skilled artisan will be aware of various techniques for achieving this. For example, the antibody can be conjugated with biotin and any of the four broad categories of labels mentioned above can be conjugated with avidin, or vice versa. Biotin binds selectively to avidin and thus, the label can be conjugated with the antibody in this indirect manner. Alternatively, to achieve indirect conjugation of the label with the antibody, the antibody may be conjugated with a small hapten and one of the different types of labels mentioned above is conjugated with an anti-hapten antibody. Thus, indirect conjugation of the label with the antibody can be achieved. In some embodiments of the invention one or more secondary antibody molecules may be conjugated with a label-conjugated polymer backbone. Thus, amplification of the signal may be achieved.

Indirectly and directly labeled secondary antibodies are also commercially available. For example, one example of commercially available label-conjugated polymer backbone carrying secondary antibody molecules reagent is EnVision™ reagent (DAKO). A secondary antibody carrying a label aimed for a particular type of detection may be obtained from numerous manufacturers.

The term "specific binding" refers to the ability of a binding agent to preferentially bind to a particular analyte that is present in a homogeneous mixture of different analytes. In certain embodiments, a specific binding interaction will discriminate between desirable and undesirable analytes in a sample, in some embodiments more than about 10 to 100-fold or more (e.g., more than about 1000- or 10,000-fold).

In certain embodiments, the affinity between a binding agent and analyte when they are specifically bound in a capture agent/analyte complex is characterized by a KD (dissociation constant) of less than 10-6 M, less than 10-7 M, less than 10-8 M, less than 10-9 M, less than 10-10 M, less than 10-11 M, or less than about 10-12 M or less.

A "plurality" contains at least 2 members. In certain cases, a plurality may have at least 10, at least 100, at least 1000, at least 10,000, at least 100,000, at least 106, at least 107, at least 108 or at least 109 or more members.

Other definitions of terms may appear throughout the specification.

DETAILED DESCRIPTION

In order to further illustrate the present invention, the following specific examples are given with the understanding that they are being offered to illustrate the present invention and should not be construed in any way as limiting its scope.

As summarized above, aspects of the present disclosure include methods for determining the eligibility of a subject having a malignancy for treatment with an anti-PD therapeutic agent. In certain embodiments, the method includes determining a Combined Positive Score (CPS) for PD-L1 expression in a tumor sample from a subject. We have found that use of the disclosed CPS dramatically decreases the work load for pathologists in the clinic, is easier to apply, produces higher inter-observer and intra-observer concordances, and identifies subjects eligible for anti-PD therapy who would otherwise be missed using other scoring methods focusing solely on biomarker expression on tumor cells.

The CPS is calculated by: determining the number of viable PD-L1 positive tumor cells, the number of viable PD-L1 negative tumor cells, and the number of viable PD-L1 positive mononuclear inflammatory cells (MIC) in a tumor tissue sample from a subject having a malignancy; and calculating the CPS using the following formula:

$$CPS = \frac{\# \; PD\text{-}L1 \; \text{positive tumor cells} + \# \; PD\text{-}L1 \; \text{positive } MIC}{\# \; \text{of } PD\text{-}L1 \; \text{positive tumor cells} + PD\text{-}L1 \; \text{negative tumor cells}} \times 100\%$$

Although the score can be calculated as greater than 100%, the maximum CPS is defined as 100%. The specimen is considered PD-L1 positive (and thus the subject eligible for treatment with anti-PD therapy) if CPS is above a threshold level. Thresholds can be determined by a ROC curve for best responder/cut off (threshold) correlation. Threshold (or cut offs/cut points) can thus be any applicable CPS value, including but not limited to: 1%; 5%; 10%; 20% 30%; 40%; 50%; 60%, etc., and is specific to the drug used. In some embodiments, the threshold is set at 1%. In such embodiments, the specimen is considered PD-L1 positive if CPS ≥1% (i.e., equal to or above the threshold value). PD-L1 positive cells are viable cells (tumor or mononuclear inflammatory cells) that exhibit membrane staining at any intensity over background.

PD-L1 expression of the specimen is determined by the Combined Positive Score (CPS). In certain embodiments, the tissue sample (or specimen) must contain a minimum number of viable cells for evaluation, e.g., at least 50 viable tumor cells, at least 100 viable tumor cells, at least 150 viable tumor cells, at least 250 viable tumor cells, etc. By viable cells is meant that the cells were viable at the time they were harvested from the subject, and not necessarily viable at the time of staining. For example, where tumor biopsy sample slides are analyzed, the cells are considered viable cells if they are deemed, upon observation and analysis, to have been viable at the time the tumor biopsy was harvested. If the specimen contains the minimum number of viable cells, the specimen is evaluable using the CPS method, e.g., by calculating an eligibility score.

Detecting PD-L1 positive cells in a tumor sample can be done in any convenient manner.

In certain embodiments, the CPS is calculated from a stained tumor tissue biopsy section (e.g., on a slide) or serial tumor tissue biopsy sections by immunohistochemistry (IHC) staining, in-situ hybridization (ISH; e.g., fluorescence-in-situ-hybridization, or FISH), histological stain, and combinations thereof. In certain embodiments, a tumor tissue biopsy section is analyzed by IHC to calculate the CPS. In certain of these embodiments, the percentage of viable PD-L1 positive and negative tumor cells and PD-L1 positive mononuclear inflammatory cells (MIC) is determined within the tumor nests and the adjacent supporting stroma. In such embodiments, cells are positive for PD-L1 staining if they display partial or complete membrane staining relative to all viable tumor cells present in the sample. It is noted here that patients with advanced-stage disease of certain tumor types (e.g., non small cell lung carcinoma (NSCLC)) are often diagnosed on a small biopsy or cytology specimen obtained through a minimally invasive procedure. These small biopsy or cytology specimens are often the only samples available for testing. The methods described herein are especially attractive for cytology specimens such as these, i.e., those in which the context of the tissue architecture is lost and it is very challenging to distinguish tumor from immune cells. Such samples include fine needle aspirates (where a thin needle is inserted into an area of abnormal-appearing tissue) or body fluid for sampling of cells. It can be the case that using CPS or a variation thereof is the only reliable method to analyze these specimens.

In other embodiments, the CPS is calculated from a tumor tissue sample that is not a fixed section on a slide. For example, in certain embodiments, the CPS is calculated using flow cytometric analysis of a cell suspension from the tumor tissue sample. In these embodiments, the tumor tissue cell suspension can be stained with a detectable PD-L1 binding agent (e.g., a fluorescently labeled antibody) and analyzed on a flow cytometer for counting the number of tumor cells and MIC cells expressing PD-L1. Tumor cells and MIC in the sample can be distinguished using any convenient flow cytometric parameter, e.g., forward scatter (FS), side scatter (SS), or by the expression of one or more additional makers using corresponding detectable binding agents for the one or more additional markers, e.g., markers specific or MIC or tumor cells. In other embodiments, the cells in the tumor tissue sample can be analyzed on a cell-by-cell basis for mRNA expression of PD-L1 and any other desired target, e.g., using single-cell nucleic acid sequencing methods for gene expression profiling (e.g., next generation sequencing methods).

As noted above, certain embodiments of the disclosed methods include staining the tumor tissue biopsy section for at least one (or multiple) additional target(s) or with a stain. Where multiple targets are assessed, e.g., a cell type-specific marker or a second tumor cell marker, the staining process may be done in a multiplex fashion, i.e., all desired markers are assessed on the same tissue sample simultaneously (e.g., using detectably distinguishable target-specific binding agents). In other embodiments, the multiple targets are detected on separate tissue samples, e.g., serial tissue sections derived from the same tumor biopsy from the subject. In embodiments where an additional stain is employed, the stain can be a histological stain, including but not limited to hematoxylin and eosin (H&E stain), which is the most commonly used light microscopy stain in histology and histopathology. Hematoxylin, a basic dye, stains nuclei blue due to an affinity to nucleic acids in the cell nucleus; eosin, an acidic dye, stains the cytoplasm pink. Another commonly performed histochemical technique is the Perls Prussian blue reaction, used to demonstrate iron deposits in diseases like hemochromatosis. In some embodiments, the tissue sample is stained with a viability stain or dye to enhance the identification of viable cells. For example, a tissue sample analyzed by flow cytometry can be contacted with a viability dye prior to analysis, e.g., propidium iodide. Any convenient viability stain may be employed, with many examples known in the art. Further, there are many other staining techniques known in to those of skill in the art that can be used to selectively stain cells and cellular components that find use in the present disclosure, and as such no limitation in this regard is intended.

The staining of a target (e.g., PD-L1) in cells from a tumor tissue biopsy is generally done by contacting the cells with one or more detectable target-specific binding agents under suitable conditions to allow for binding of the target-specific binding agent to its desired target (while minimizing non-target binding). As noted above, the term "target-specific binding agent" means any agent that specifically binds to a target or analyte of interest, e.g., a target of interest that is present in a tissue section as described herein (e.g., a polypeptide or polynucleotide). In some embodiments, the target-specific binding agent is an antibody (or target-binding fragments thereof), e.g., as used in IHC and flow cytometry. Staining may be performed with primary and secondary antibodies or without using secondary antibodies (e.g., where the primary antibody is detectably labeled). Non limiting examples of anti-PD-L1 antibodies include, but are not limited to, clone 22C3 (Merck & Co.), clone 28-8 (Bristol-Myers Squibb), and clones SP263 or SP142 (Spring Biosciences). In certain other embodiments, the target-specific binding agent is a nucleic acid or nucleic acid binding agent, e.g., as employed in in situ hybridization (ISH) reactions. For example, the target binding reagent can be a DNA, RNA, DNA/RNA hybrid molecule, peptide nucleic acid (PNA), and the like. No limitation in the metes and bounds of a target-specific binding agent that finds use in the subject disclosure is intended.

The target-specific binding agent (or any secondary reagent used to detect the target-specific binding agent) may be attached to any suitable detectable label (or chromogen) or enzyme capable of producing a detectable label. Thus, in certain embodiments, the first or second label is produced by an enzymatic reaction, e.g., by the activity of horseradish peroxidase, alkaline phosphatase, and the like. Any convenient enzymatic label/chromogen deposition system can be employed (e.g., as used in standard IHC methods), and as such, no limitation in this regard is intended. In some embodiments, the detectable label is a fluorescent tag.

In some embodiments, the staining reagents used may include a target-specific antibody (e.g., a PD-L1 specific antibody). Where an additional target is to be detected, the staining reagents used may include one or more additional antibodies that each bind to a different antigen. For example, a set of antibodies may include a first antibody that binds to a first antigen (e.g., PD-L1), a second antibody that binds to a second antigen, a third antibody that binds to a third antigen and, optionally a fourth antibody that binds to a fourth antigen and/or further antibodies that bind to further antigens. In some embodiments, the antibody/antibodies used are primary antibodies that are detected by use of a secondary antibody (or other reagent). The staining steps thus may be done by incubating the cells of the tissue sample, e.g., a tissue section or cell suspension, with the primary antibody/antibodies and then, after the primary antibody has bound to the desired target in/on the cells, incubating the cells with the labeled secondary antibody/ antibodies (e.g., as is done in standard IHC protocols). In some multiplex embodiments, each of the primary antibodies for each different target is from a different species (e.g., goat, rabbit, mouse, camel, chicken, donkey, etc.) and the corresponding secondary antibodies specific for each different primary antibody are distinguishably labeled from each other.

In some multiplex embodiments, the first and second (and subsequent) targets being detected are different from each other, e.g., are different proteins or polynucleotides (e.g., different genes). However, in some multiplex embodiments, there may be some overlap. For example, in certain cases, a first target-specific binding agent may bind to the same target as a second target-specific binding agent but at a different epitope or site.

As noted above, the tissue sample (e.g., tissue section or cell suspension) can be assessed for targets other than PD-L1. In certain embodiments, the additional target is one that identifies tumor cells. Examples include, but are not limited to: cytokeratin markers including pan-CK cocktails, (e.g., AE1/AE3, CAM5.2/AE1) for adenocarcenomas and CK903 (34βE12) for squamous cell carcinomas. In certain embodiments, the additional target is one that identifies MIC. Examples include, but are not limited to: CD3, CD5, CD4, CD7, CD8, CD20, and other markers of MIC.

In certain embodiments, the sample being analyzed is a tissue section, e.g., a formalin fixed and paraffin embedded (FFPE) tissue section. In alternative embodiments, the tissue section has been fixed in a different way, including tissue sections that have been fixed in, e.g., acrolein, glyoxal, smium tetroxide, arbodiimide, mercuric chloride, zinc salts, picric acid, potassium dichromate, ethanol, methanol, acetone, and/or acetic acid.

In embodiments in which a tissue section is analyzed by microscopy, the method further comprises comparing the relative location of the detected first (or any subsequent) label on the tissue section(s). This can be done, for example, by overlaying multiple images of the slide or series of slides that were collected during the analysis (e.g., for different labels). For example, one or more images collected for the labels of a first tissue section (or first label) can be overlaid onto one or more images collected for a second adjacent tissue section (or second, distinguishable label).

In certain embodiments, the images may be overlaid and analyzed to identify the boundaries of individual cells or regions in the tissue section, and/or subcellular features in individual cells, in the image. Computer-implemented methods for segmenting images of cells and tissues are known in the art and range from relatively simple thresholding techniques (see, e.g., Korde et al. Anal Quant Cytol Histol. 2009 31: 83-89 and Tuominen et al. Breast Cancer Res. 2010 12: R56), to more sophisticated methods, such as, for instance, adaptive attention windows defined by the maximum cell size (Ko et al. J Digit Imaging. 2009 22: 259-274) or gradient flow tracking (Li, et al. J Microsc. 2008 231: 47-58). Some suitable image segmentation methods may be reviewed in Ko et al. (J Digit Imaging. 2009 22: 259-74) and Ong et al. (Comput Biol Med. 1996 26:269-79). Next the data that corresponds to each of the individual parameters that have been defined by the segmenting are integrated to provide, for each cell, values that indicate which markers are associated with the cell. In certain cases, a cell may be identified as being malignant, non-malignant, infiltrating non-malignant, etc., as a result of this analysis. This data may allow one to potentially type the cells in the sample. As such, this method may comprise displaying an image of the sample, in which the cells are color-coded by their type.

In certain embodiments, the tissue section may be a section of a tissue biopsy obtained from a patient, e.g., a patient having a malignancy. Biopsies of interest include both tumor and non-neoplastic biopsies of skin (melanomas, carcinomas, etc.), soft tissue, bone, breast, colon, liver, kidney, adrenal, gastrointestinal, pancreatic, gall bladder, salivary gland, cervical, ovary, uterus, testis, prostate, lung, thymus, thyroid, parathyroid, pituitary (adenomas, etc.), brain, spinal cord, ocular, nerve, and skeletal muscle, etc. In certain embodiments, the subject from which the biopsy is obtained has a malignancy is selected from: gastric cancer, esophageal carcinomas, head and neck cancer (e.g., head and neck squamous cell carcinoma, or HNSCC), renal cell carcinoma, urothelial/bladder carcinoma, ovarian carcinoma, myeloma, melanoma, lung cancer, classical Hodgkin's lymphoma, and breast cancer (e.g., triple negative breast cancer, hormone receptor positive (ER and/or PR) and Her2 positive breast cancer), small cell lung cancer, salivary gland carcinoma, vulvar carcinoma, thyroid carcinoma, anal canal carcinoma, biliary carcinoma, mesothelioma, cervical carcinoma, and neuroendocrine carcinoma.

In some embodiments, the method may involve obtaining one or more image as described above (e.g., an electronic form of which may have been forwarded from a remote location) and may be analyzed by a doctor or other medical professional to calculate the CPS. In other embodiments, the tissue sections are assessed in real time, i.e., not from a stored image of the slide (or other form of stored data). In some embodiments, a slide or image of the slide, as described above, is assessed and a CPS is calculated in an automated fashion in silico, e.g., without the slide(s) or image(s) of the slide being assessed by a human. In such embodiments, the slide(s)/image(s) are analyzed by a computer that has been programmed to analyze the staining pattern and identify the PD-L1 positive and negative tumor cells as well as the PD-L1 positive MICs. In other embodiments, the image of the slide or slides is annotated by a slide imaging device such that cells of each different cell type (e.g., PD-L1 positive tumor, PD-L1 negative tumor, and PD-L1 positive MIC) are readily identifiable by a user, e.g., by color coding of the cells or regions in the image.

In any embodiment, data can be forwarded to a "remote location," where "remote location" means a location other than the location at which the image is examined. For example, a remote location could be another location (e.g., office, lab, etc.) in the same city, another location in a different city, another location in a different state, another location in a different country, etc. As such, when one item is indicated as being "remote" from another, what is meant is that the two items can be in the same room but be separated, or at least in different rooms or different buildings, and can be at least one mile, ten miles, or at least one hundred miles apart. "Communicating" information references transmitting the data representing that information as electrical signals over a suitable communication channel (e.g., a private or public network). "Forwarding" an item refers to any means of getting that item from one location to the next, whether by physically transporting that item or otherwise (where that is possible) and includes, at least in the case of data, physically transporting a medium carrying the data or communicating the data. Examples of communicating media include radio or infra-red transmission channels as well as a network connection to another computer or networked device, and the internet or include email transmissions and information recorded on websites and the like. In certain embodiments, the image may be analyzed by an MD or other qualified medical professional, and a report based on the results of the analysis of the image may be forwarded to the patient from which the sample was obtained.

Specific Embodiments

The specific embodiments below are intended for illustration purposes only and are not intended to be limiting.

The purpose of these embodiments is to provide guidelines for evaluating PD-L1 expression on formalin-fixed, paraffin-embedded (FFPE) tumor tissue section with Dako's PD-L1 IHC 22C3 pharmDx kit (SK006). This immunohistochemical (IHC) assay is performed using the Dako Autostainer Link 48 automated staining system.

The embodiments below are described with respect to the use of the PD-L1 IHC 22C3 pharmDx kit, which is a qualitative immunohistochemical assay using Monoclonal Mouse Anti-PD-L1, Clone 22C3. This kit is intended for use in the detection of PD-L1 protein in formalin-fixed, paraffin-embedded (FFPE) tumor tissue using EnVision FLEX visualization system on Autostainer Link 48. Here, PD-L1 protein expression is used to determine a Combined Positive Score (CPS; as describe above). In these embodiments, the specimen is considered PD-L1 positive if the CPS ≥1%, where PD-L1 positivity is defined as a viable cell exhibiting membrane staining with the 22C3 antibody at any intensity (as compared to positive and negative controls, as described below).

PD-L1 IHC 22C3 pharmDx is indicated as an aid in identifying patients having a malignancy for treatment with KEYTRUDA® (pembrolizumab) (e.g., patients with gastric carcinoma or HNSCC).

Definitions

| Word/Acronym | Definition of Word/Word(s) for Acronym |
| --- | --- |
| CPS | Combined Positive Score |
| H&E | Hemotaxylin and eosin |
| MCF-7 | PD-L1-negative control cell line |
| MIC | Mononuclear inflammatory cells |
| NCI-H226 | PD-L1-positive control cell line |
| NCR | Negative Control Reagent |
| PD-L1 | Programmed Death Ligand 1 |

Clinical Interpretation Guidelines for PD-L1 IHC 22C3 pharmDx in TumorTissue Specimen Criteria A hemotaxylin and eosin (H&E) stained section is recommended for the evaluation of an acceptable tumor tissue sample. PD-L1 IHC 22C3 pharmDx and the H&E staining is performed on serial sections from the same paraffin block of the specimen to confirm:

1. The histological diagnosis of the cancer/malignancy.

2. The specimen contains a minimum of 100 viable tumor cells to determine the percentage of positive cells. For patient specimens with less than 100 viable tumor cells, tissue from a deeper level of the block, or potentially another block, could present sufficient number of viable tumor cells for PD-L1 IHC 22C3 pharmDx testing.

3. The specimen has been properly fixed and prepared for IHC analysis. Well-preserved and well-stained areas of the specimen are used to make a determination of the percentage of cells present (e.g, PD-L1 positive tumor cells).

Evaluating Controls

Deviations in the recommended procedures for tissue fixation, processing and embedding in the user's laboratory may produce significant variability in results. Therefore, the following controls can be included in each staining run.

| Quality Control Summary | | |
| --- | --- | --- |
| Control Type | Reagents Used in Testing | Purpose of Testing |
| Control Slide supplied by Dako | Primary Antibody, *Negative Control Reagent & Detection System | Controls staining procedure only |
| Positive Control: Tissue or cells containing target antigen to be detected. The ideal control is weakly positive staining tissue, which may be more sensitive in detecting reagent degradation. | Primary Antibody, Negative Control Reagent & Detection System | Controls all steps of the analysis. Validates reagents and procedures used for PD-L1 staining. |
| Negative Control: Tissues or cells expected to be negative (could be located in patient tissue or positive control tissue). | Primary Antibody, Negative Control Reagent & Detection System | Detection of unintended antibody cross-reactivity to cells/cellular components. |
| Patient tissue slide | Negative Control Reagent & same Detection System as used with the Primary Antibody | Detection of non-specific background staining. |

*From the same species as the primary antibody, but not directed against the same target antigen. To detect non-specific antibody binding, e.g. binding of Fc portion of antibody by the tissue.

All control tissues must meet acceptance criteria to proceed with evaluation of PD-L1 staining on gastric carcinoma tissues. (See FIG. 1 for an example of the Rules to follow when evaluating controls.)

PD-L1 IHC 22C3 pharmDx Control Cell Line Slide

Examine the PD-L1 IHC 22C3 pharmDx control cell line slide to determine that reagents are functioning properly. Each slide contains sections of cell pellets with positive and negative PD-L1 expression. Assess the percentage of positive cells and the staining intensity. If any staining of the control cell line slide is not satisfactory, all results with the specimens should be considered invalid. Control cell line slide is not used as an aid in interpretation of patient results.

Evaluate the overall staining intensity using the following guide:

| | |
|---|---|
| 0 | Negative |
| 1+ | Weak Intensity |
| 2+ | Moderate Intensity |
| 3+ | Strong Intensity |

Figure 2:
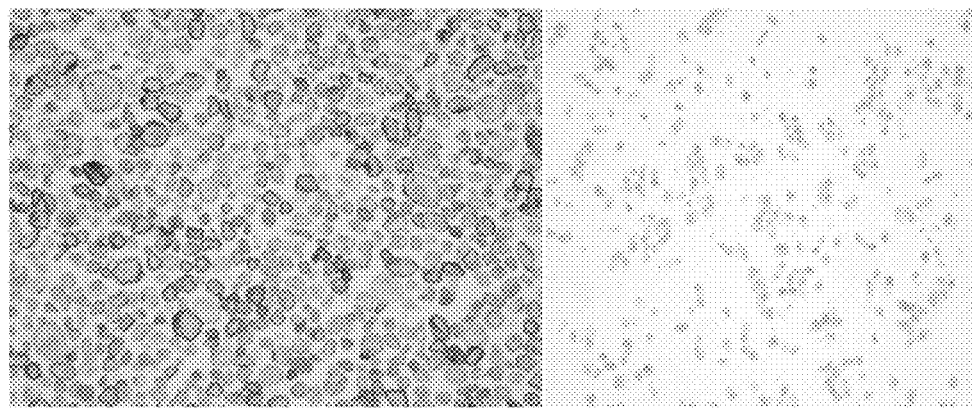
FIG. 2 provides images of positive (left panel) and negative (right panel) control cell staining.

FIG. 2 shows representative PD-L1 positive (left panel) and negative (right panel) control cell line staining. The PD-L1 positive cell line NCI-H226 and the negative control cell line is MCF-7. As seen in this figure, at least 70% of the PD-L1 positive control cells contain cell membrane staining of at least 2+ average staining intensity and any non-specific staining is <1+ staining intensity. For the PD-L1 negative cell pellet, the majority of cells demonstrate no staining. (The presence of 10 or fewer cells with distinct cell membrane staining in the negative control cell sample is generally acceptable). Any non-specific staining is <1+ staining intensity.

User-Provided Control Tissue Slides

A user-provided positive control tissue slide is examined after the control cell line slides described above. This slide verifies that the fixation method and epitope retrieval process are effective. The ideal positive control tissue provides a complete dynamic representation of weak to moderate cell membrane staining of tumor cells and/or cell membrane/cytoplasmic staining of tumor-associated mononuclear inflammatory cells (MICs). Use intact cells for interpretation of staining results because necrotic or degenerated cells often stain non-specifically. Non-specific staining should be ≤1+.

A user-provided negative control tissue slide is also examined to verify the specificity of the labeling of the target antigen by the primary antibody. The ideal negative control tissue demonstrates no staining on tumor cells and MICs. The absence of specific staining in the negative control tissue slide confirms the lack of kit cross-reactivity to cells/cellular components. The variety of different cell types present in most tissue sections offers internal negative control sites; this should be verified by the user.

If staining of positive and/or negative control tissues are not satisfactory, the results with the patient specimen should be considered invalid.

In addition, patient specimens are stained with a Negative Control Reagent (NCR) from the PD-L1 IHC 22C3 pharmDx kit. Specimens stained with the NCR should have 0 specific staining and ≤1+ non-specific staining. Staining occurring in the cytoplasm of tumor cells of the specimen treated with the NCR should be considered non-specific staining.

Example of Scoring Guidelines

For evaluation of tissue section staining and scoring (e.g., using IHC), an objective of 10-20× magnification is used. Partial or complete cell membrane staining of tumor cells that is perceived distinct from cytoplasmic staining is considered positive, as is cell membrane/cytoplasmic staining of MICs within the tumor nests and the adjacent supporting stroma. Adjacent MICs are defined as being within the same 20× field as the tumor. However, MICs that are NOT directly associated with the response against the tumor should be excluded. For example, in some cases, MICs are in the 20× field of view but can clearly be directly linked to non-tumor related causes. Such MICs should be excluded from scoring.

Refer to the table below for details in evaluating PD-L1 positivity.

| Element | Included in Scoring | Excluded from Scoring |
|---|---|---|
| Tumor cells | Convincing partial or complete membrane staining (at any intensity) of viable carcinoma tumor cells | Tumor cell cytoplasmic staining |
| Immune cells | Membrane and/or cytoplasmic* staining (at any intensity) of mononuclear inflammatory cells (MIC) within tumor nests and adjacent supporting stroma**, such as:<br>Lymphocytes (lymphocyte aggregates)<br>Monocytes<br>Macrophages | Immune cells not infiltrating nor adjacent to tumor<br>Normal cells adjacent to tumor cells<br>Stromal cells (fibroblasts)<br>Necrotic cells and/or cellular debris that may stain PD-L1 positive<br>Plasma cells<br>Neutrophils |
| Morphology Patterns | N/A | Tissue damage/immune cells not responsive to tumor (e.g., chronic inflammation) |

*Lymphocytes often present indistinctive staining of membrane and cytoplasm due to a high nuclear to cytoplasmic ratio. Therefore, membrane and/or cytoplasmic staining in lymphocytes shall be included in the score.

**Adjacent MICs are defined as being within the same 20x field as the tumor. However, MICs that are NOT directly associated with the response against the tumor should be excluded.

Examples for Simple Calculations of CPS

Example 1: Calculate CPS for a specimen containing 100 total tumor cells, 80 positive tumor cells, and 50 positive adjacent MICs.

$$CPS = \frac{80 \text{ positive tumor cells} + 50 \text{ positive } MICs}{100 \text{ total tumor cells}} \times 100\%$$

In this case the CPS=100% (although the score is greater than 100%, the maximum CPS is defined as 100%). The specimen is thus scored as PD-L1 Positive, and as such the subject is considered as eligible for anti-PD therapy.

Example 2: Calculate CPS for a specimen containing 1000 total tumor cells, 0 positive tumor cells, 10 positive adjacent MICs.

$$CPS = \frac{0 \text{ positive tumor cells} + 10 \text{ positive } MICs}{1000 \text{ total tumor cells}} \times 100\%$$

In this case the CPS=1%. The specimen is thus scored as PD-L1 Positive (the threshold is 1% in this example), and as such the subject is considered as eligible for anti-PD therapy.

Example 3: Calculate CPS for a specimen containing 1000 total tumor cells, 5 positive tumor cells, and 0 positive adjacent MICs.

$$CPS = \frac{5 \text{ positive tumor cells} + 0 \text{ positive } MICs}{1000 \text{ total tumor cells}} \times 100\%$$

In this case the CPS=0.5%. The specimen is thus scored as PD-L1 Negative, and as such the subject is not considered as eligible for anti-PD therapy.

Examples of More Complex Tissue Stains

Figure 3:
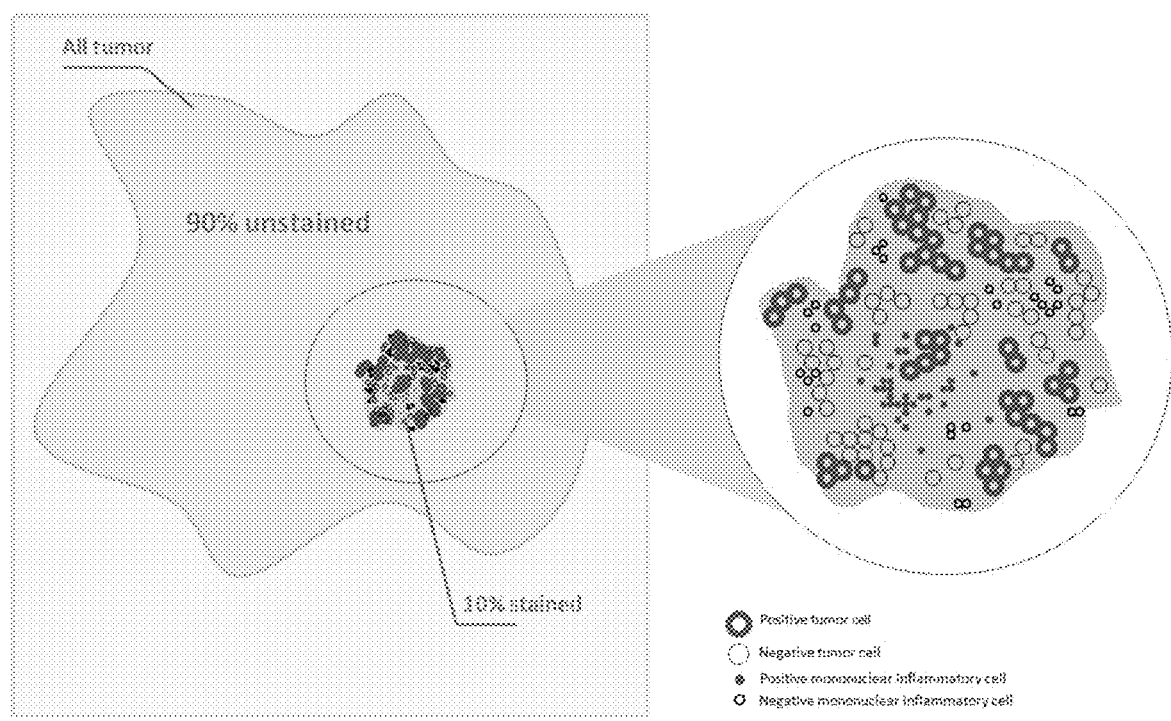
FIG. 3 provides a cartoon of a tissue section with a small staining area.

Example 1: Calculation of Combined Positive Score in a Small Tumor Area with Staining FIG. 3 shows a cartoon of a tissue section with a small staining area. At lower magnification (left), only about 10% of the tissue area is stained (90% of the tissue area is without staining). To calculate the CPS, the stained area is evaluated at a higher magnification (right) to estimate the number of PD-L1 positive and negative tumor cells and mononuclear inflammatory cells that are PD-L1 positive. In this area, 50 out of 100 tumor cells are PD-L1 positive, and there are 34 mononuclear inflammatory cells that are PD-L1 positive. The CPS score of the stained area is thus:

$$\frac{50 \text{ positive tumor cells} + 34 \text{ positive } MICs}{100 \text{ tumor cells}} \times 100 = 84\%$$

Because only 10% of the sample was stained, the CPS score is adjusted by multiplying the CPS of the stained area with the percentage of the tissue that was stained (in this case, 10%). The CPS score for the entire tissue sample is thus 10%×84%=8.4%. This specimen is thus above the threshold of 1% and is considered PD-L1 positive (and thus the subject is eligible for anti-PD therapy).

Example 2: Calculation of Combined Positive Score in a Heterogeneous Tumor Area

Figure 4:
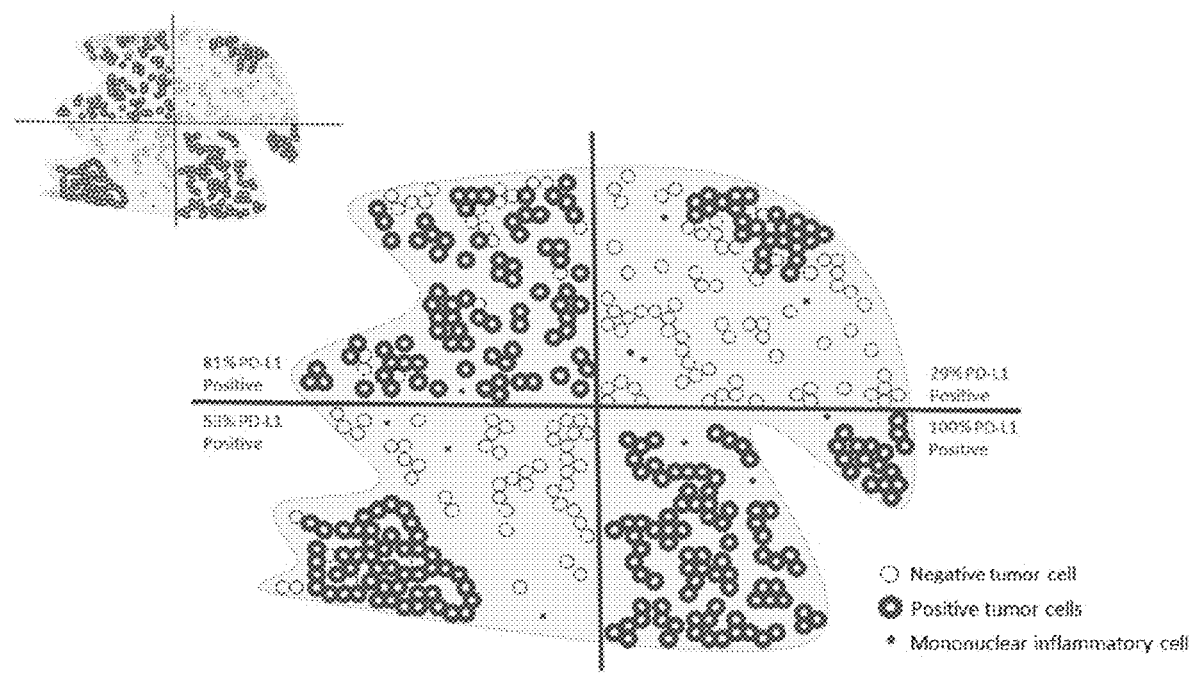
FIG. 4 provides a cartoon of a tissue section with a heterogenous tumor area.

FIG. 4 shows a cartoon of a tissue section with a heterogenous tumor area. At lower magnifications (upper left), the tissue sample is visually divided into sections. A CPS for each section is determined by observing them at higher magnification (lower right). CPS for each of the four respective sections is as follows (clockwise from top left: 81%, 29%, 100%, and 53%. To get an overall CPS, these four scores are averaged, giving an overall CPS of 65%. This specimen is thus above the threshold of 1% and is considered PD-L1 positive (and thus the subject is eligible for anti-PD therapy).

Examples of Images for Interpretation of PD-L1 IHC 22C3 pharmDx Staining

FIGS. 5 through 18 provide examples of images of tissue sections stained with the PD-L1 IHC 22C3 pharmDx kit.

Figure 5:
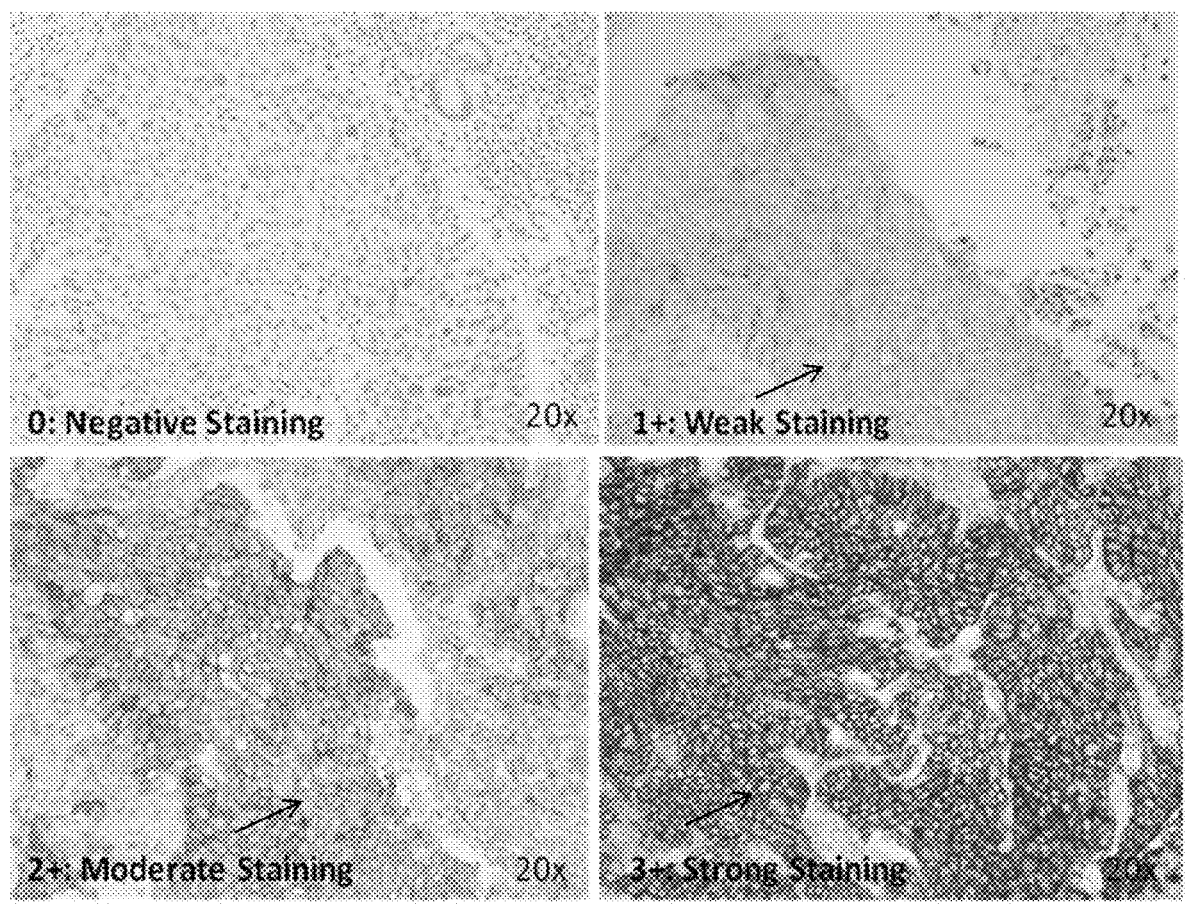
FIG. 5 provides images of a stained tissue sections showing different intensities of PD-L1 on tumor cells. Top left panel shows negative staining; top right panel shows weak staining; bottom left panel shows moderate staining; and bottom right panel shows strong staining. Arrows indicate stained cells in the relevant panels.

FIG. 5 provides an image of a stained tissue section showing different intensities of PD-L1 on tumor cells.

Figure 6:
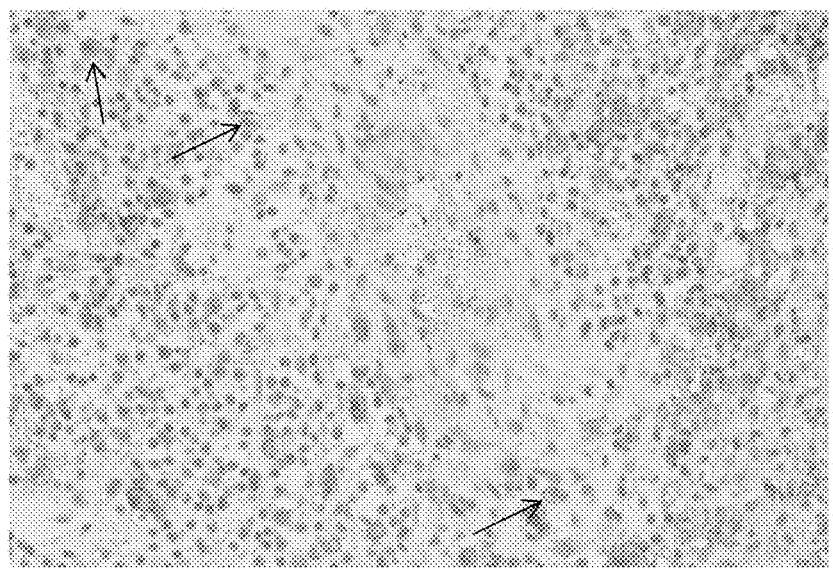
FIG. 6 provides an image of a stained tissue section showing PD-L1 positive inflammatory cells. Arrows indicate positively stained cells.

FIG. 6 provides an image of a stained tissue section showing PD-L1 positive inflammatory cells.

Figure 7:
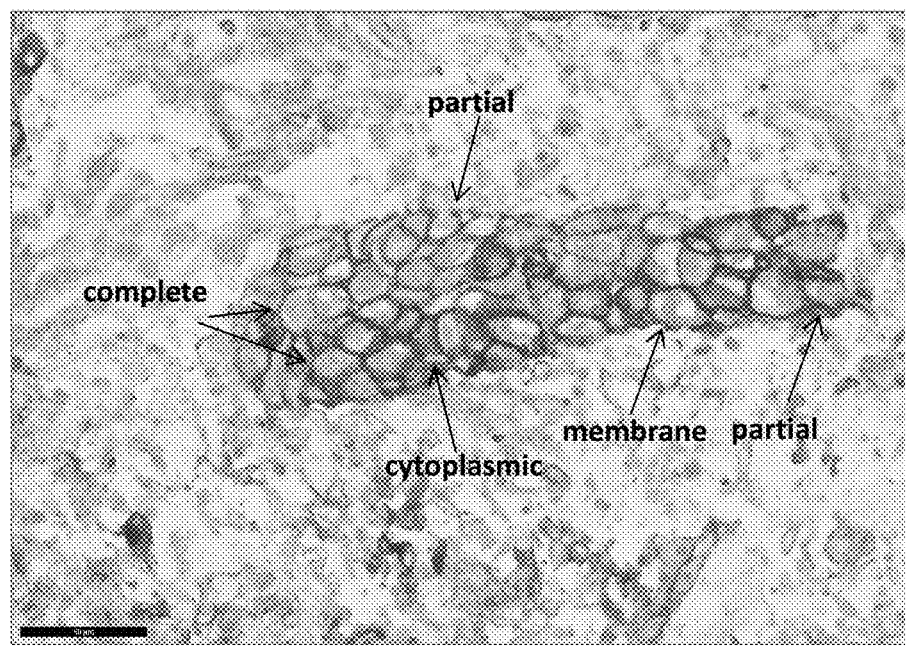
FIG. 7 provides an image of a stained tissue section showing cytoplasmic and membrane staining. Labeled arrows show complete staining, partial staining, cytoplasmic staining, and membrane staining.

FIG. 7 provides an image of a stained tissue section showing cytoplasmic and membrane staining. Labeled arrows show complete staining, partial staining, cytoplasmic staining, and membrane staining.

Figure 8:
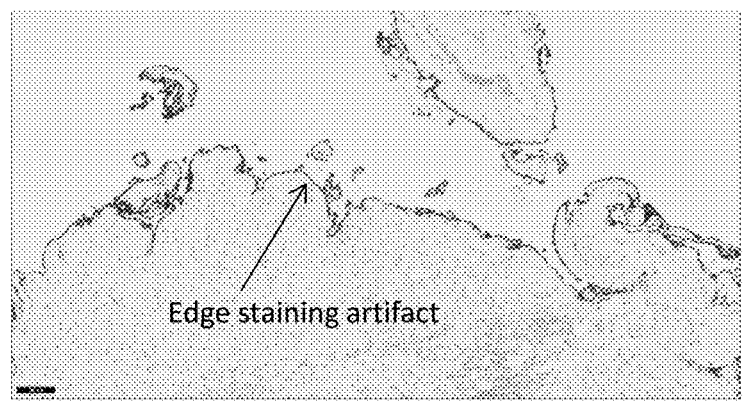
FIG. 8 provides an image of a stained tissue section showing an edge-staining artifact (example of artifact indicated by arrow).

FIG. 8 provides an image of a stained tissue section showing an edge-staining artifact (example of artifact indicated by arrow).

Figure 9:
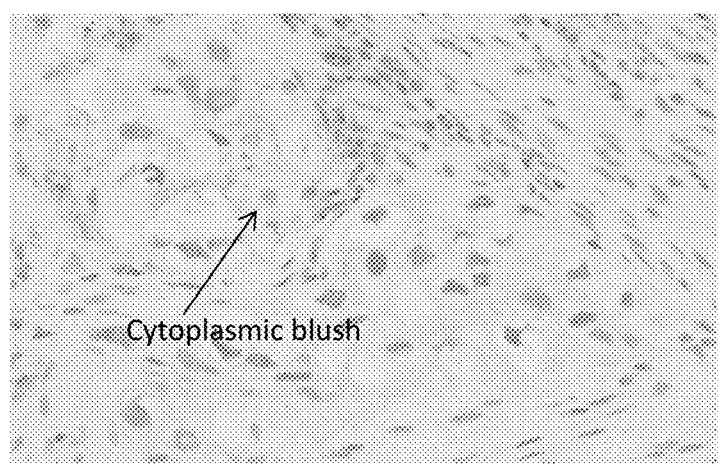
FIG. 9 provides an image of a stained tissue section showing a cytoplasmic blush artifact (example of artifact indicated by arrow).

FIG. 9 provides an image of a stained tissue section showing a cytoplasmic blush artifact (example of artifact indicated by arrow).

Figure 10:
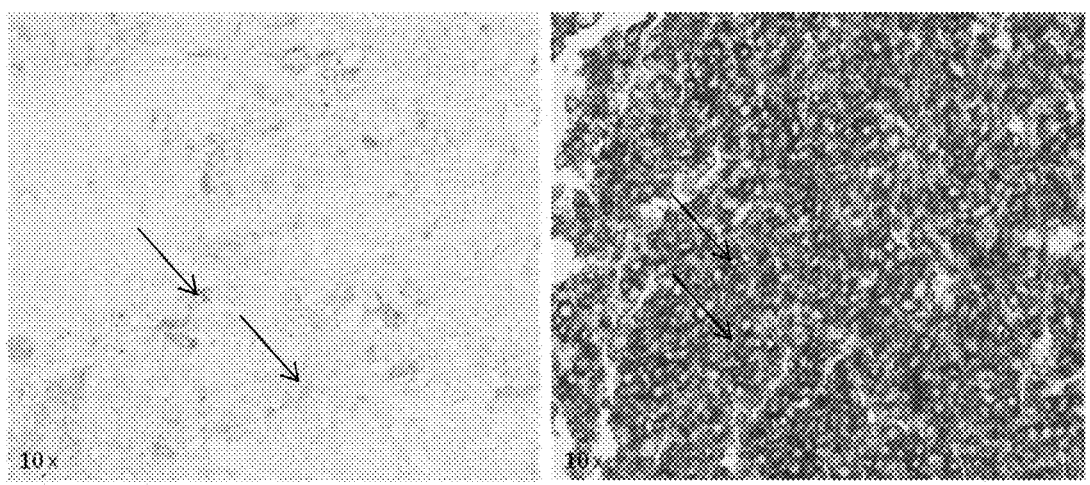
FIG. 10 provides an image of a stained tissue section showing the artifact of staining of necrotic tissue (examples of artifact indicated by arrows).

FIG. 10 provides an image of a stained tissue section showing the artifact of staining of necrotic tissue (examples of artifact indicated by arrows).

Figure 11:
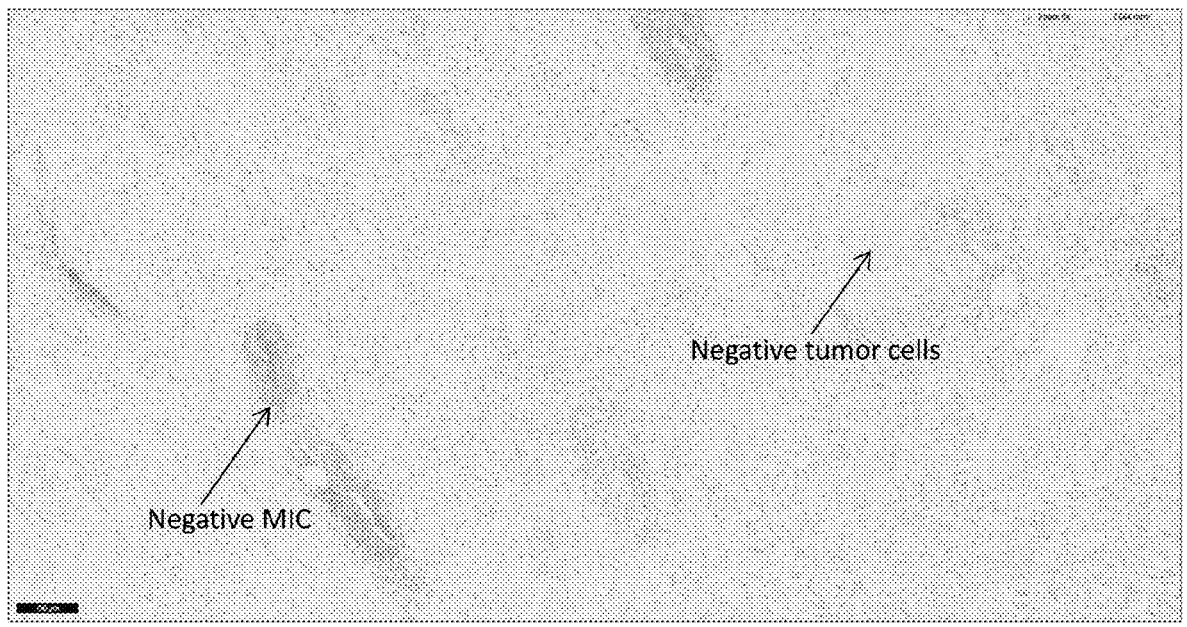
FIG. 11 provides an image of a stained tissue section showing an example of HNSCC with a CPS of 0%. Examples of negative MIC and tumor cells are indicted with arrows.

FIG. 11 provides an image of a stained tissue section showing an example of HNSCC with a CPS of 0%. Examples of negative MIC and tumor cells are indicted with arrows.

Figure 12:
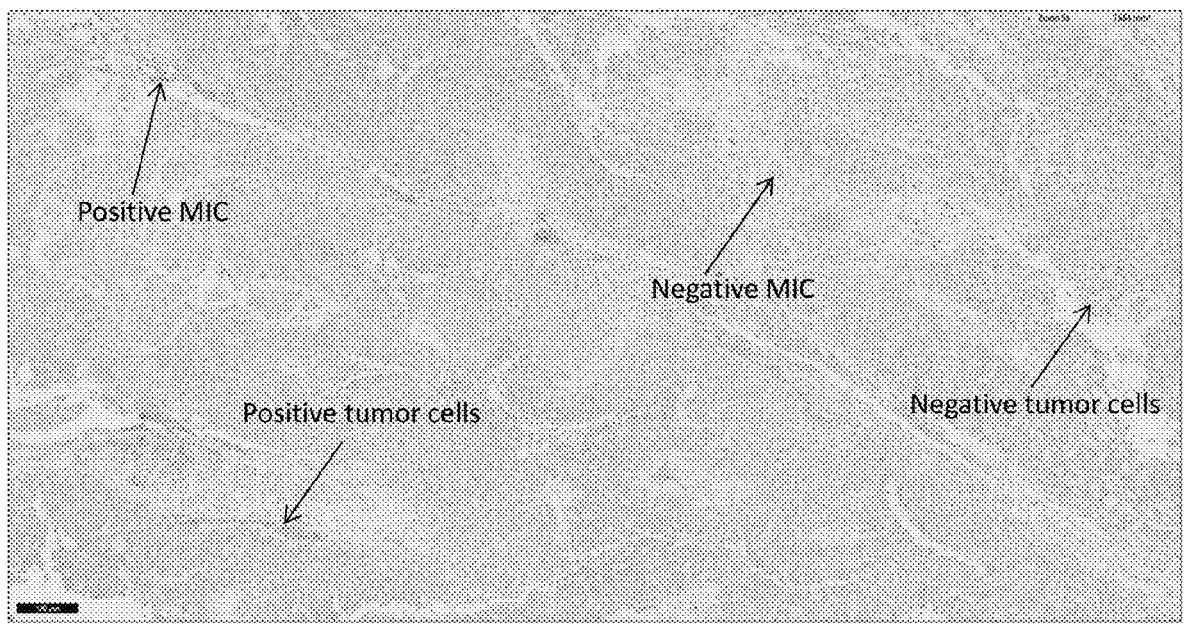
FIG. 12 provides an image of a stained tissue section showing Example of HNSCC with a CPS of 1%. Examples of negative and positive MICs and tumor cells are indicated with arrows.

FIG. 12 provides an image of a stained tissue section showing Example of HNSCC with a CPS of 1%. Examples of negative and positive MICs and tumor cells are indicated with arrows.

Figure 13:
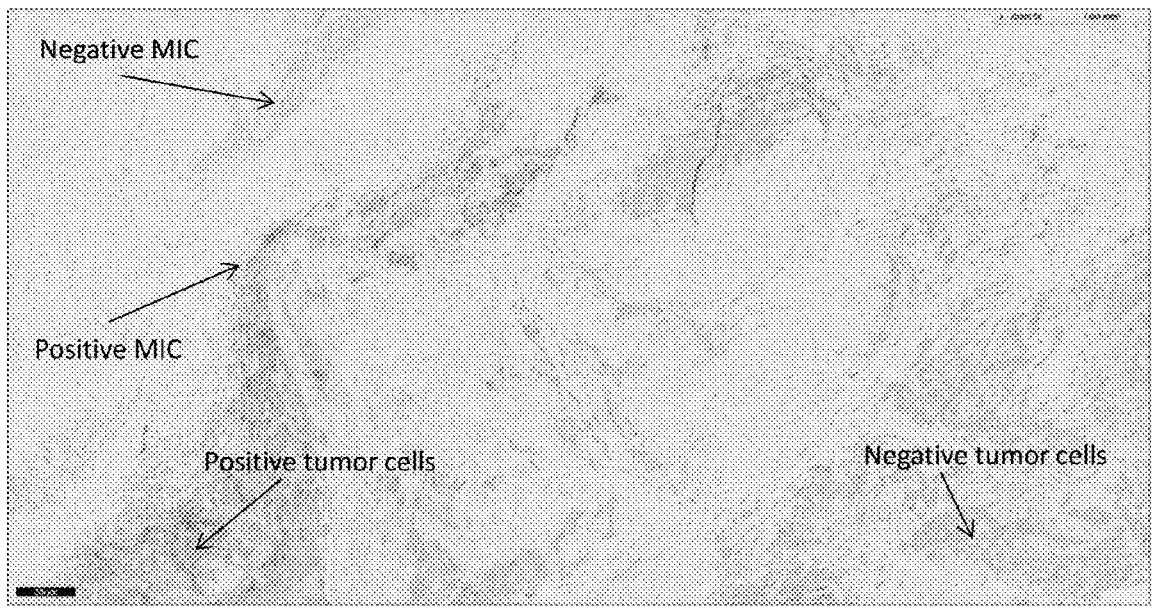
FIG. 13 provides an image of a stained tissue section showing Example of HNSCC with a CPS of 55%. Examples of negative and positive MICs and tumor cells are indicated with arrows.

FIG. 13 provides an image of a stained tissue section showing Example of HNSCC with a CPS of 55%. Examples of negative and positive MICs and tumor cells are indicated with arrows.

Figure 14:
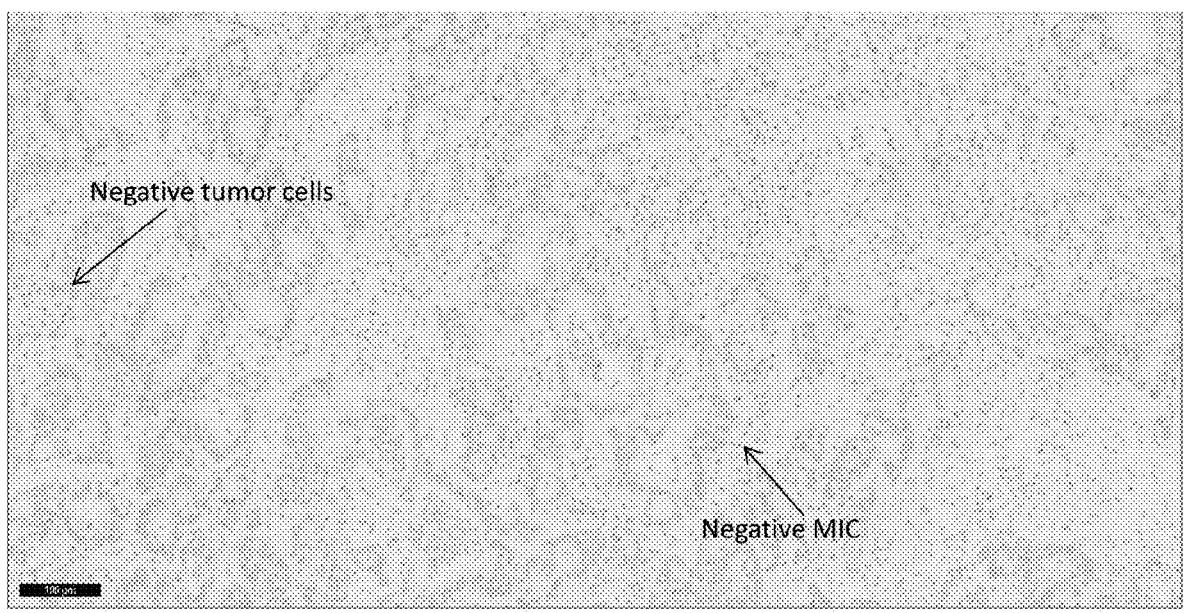
FIG. 14 provides an image of a stained tissue section showing Example of Gastric Carcinoma with a CPS of 0%. Examples of negative MIC and tumor cells are indicted with arrows.

FIG. 14 provides an image of a stained tissue section showing Example of Gastric Carcinoma with a CPS of 0%. Examples of negative MIC and tumor cells are indicted with arrows.

Figure 15:
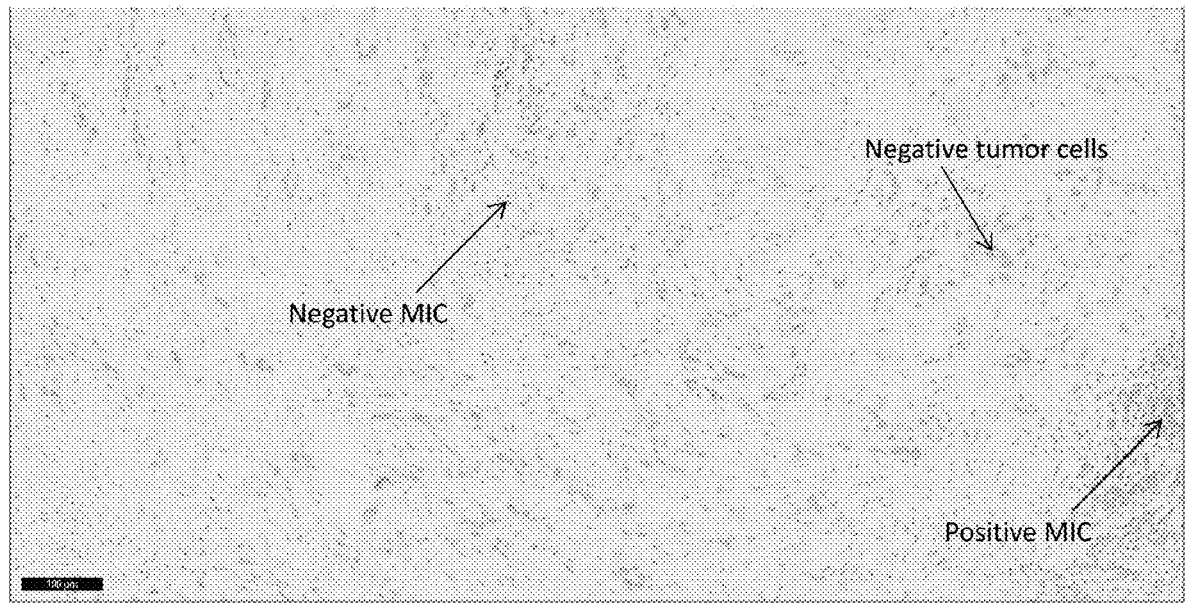
FIG. 15 provides an image of a stained tissue section showing Example of Gastric Carcinoma with a CPS of 1%. Examples of negative and positive MICs and negative tumor cells are indicted with arrows.

FIG. 15 provides an image of a stained tissue section showing Example of Gastric Carcinoma with a CPS of 1%. Examples of negative and positive MICs and negative tumor cells are indicted with arrows.

Figure 16:
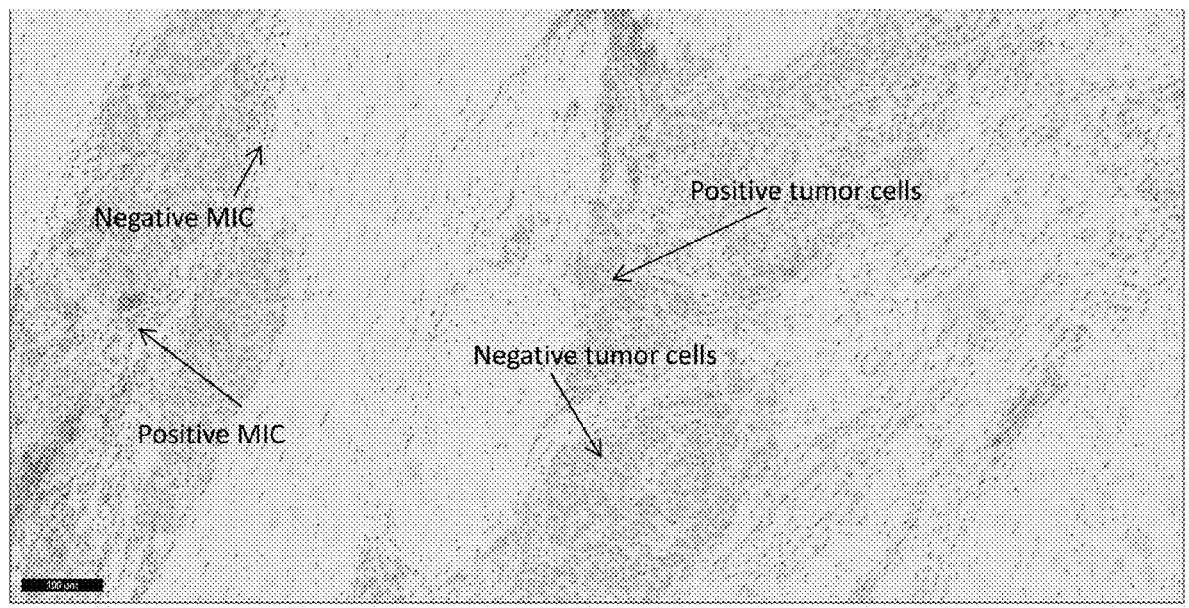
FIG. 16 provides an image of a stained tissue section showing Example of Gastric Carcinoma with a CPS of 10%. Examples of negative and positive MICs and tumor cells are indicated with arrows.

FIG. 16 provides an image of a stained tissue section showing Example of Gastric Carcinoma with a CPS of 10%. Examples of negative and positive MICs and tumor cells are indicated with arrows.

Figure 17:
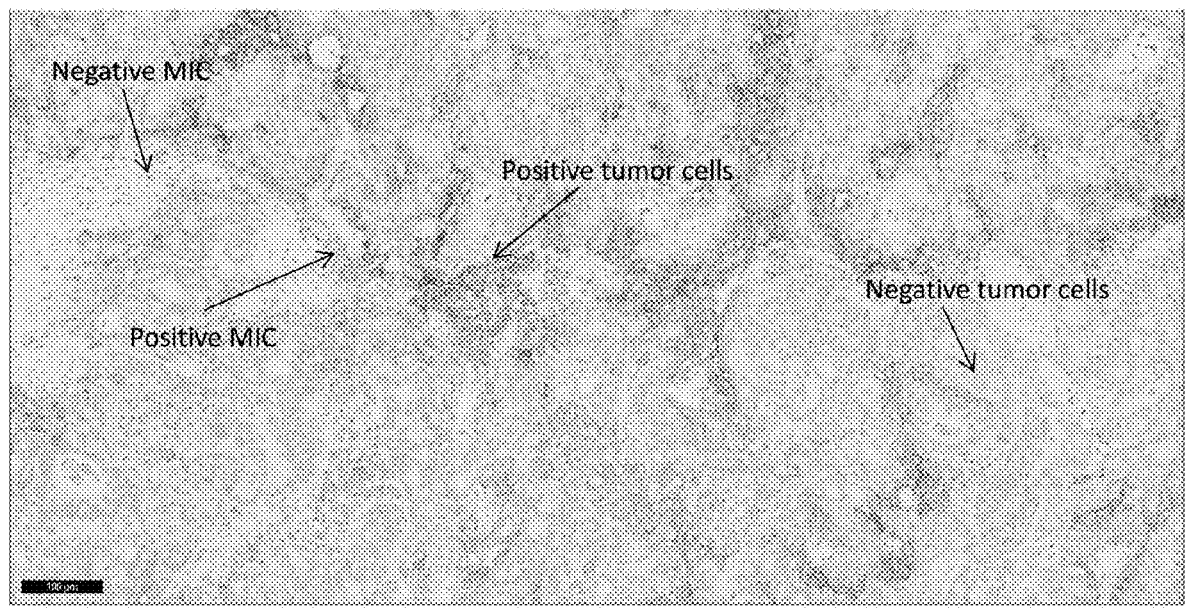
FIG. 17 provides an image of a stained tissue section showing Example of Gastric Carcinoma with a CPS of 40%. Examples of negative and positive MICs and tumor cells are indicated with arrows.

FIG. 17 provides an image of a stained tissue section showing Example of Gastric Carcinoma with a CPS of 40%. Examples of negative and positive MICs and tumor cells are indicated with arrows.

Figure 18:
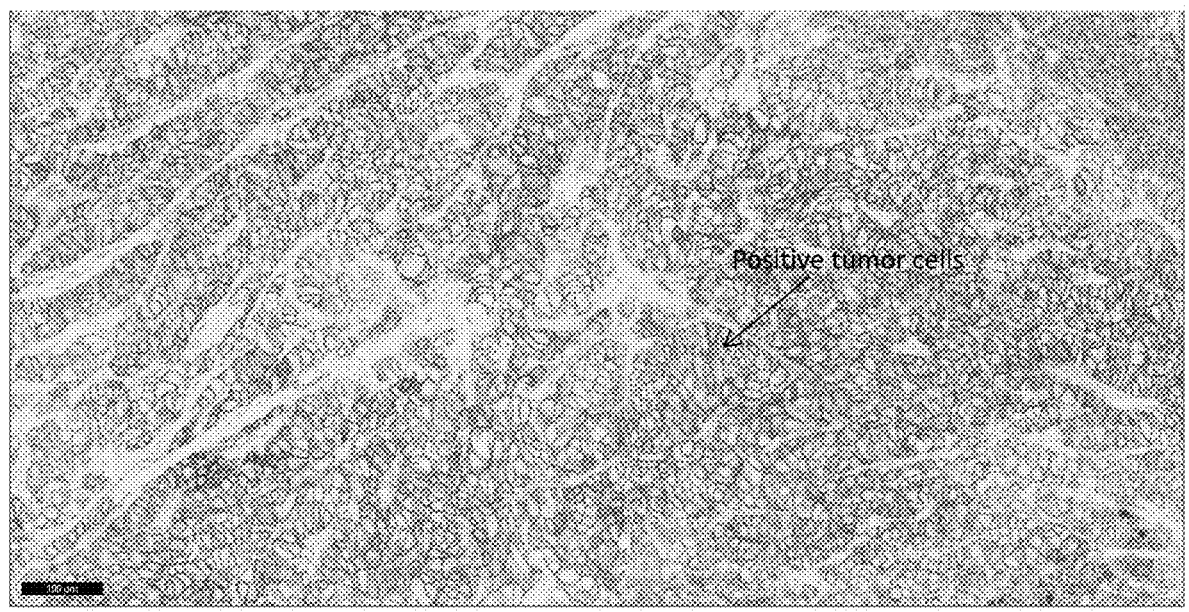
FIG. 18 provides an image of a stained tissue section showing Example of Gastric Carcinoma with a CPS of 100%. Example of positive tumor cell is indicated with an arrow.

FIG. 18 provides an image of a stained tissue section showing Example of Gastric Carcinoma with a CPS of 100%. Example of positive tumor cell is indicated with an arrow.

Kits

Also provided by this disclosure are kits that provide reagents for analyzing a tissue section(s) for determining the eligibility of a subject having a malignancy for treatment with an anti-PD therapeutic agent according to the methods described herein.

For example, a kit may contain a detectable PD-L1 specific binding agent and instructions for determining and/or calculating a combined positive score (CPS). The instructions can thus include descriptions for sample analysis, for interpreting the results of the test, and/or for calculating a CPS score to determine the eligibility of a subject having a malignancy for treatment with an anti-PD therapeutic agent, e.g., an anti-PD-L1 antibody therapy. Such instructions for practicing the subject methods and interpreting the results are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging), etc. In other embodiments, the instructions are present as an electronic storage data file present on a suitable computer readable storage medium, e.g., CD-ROM, diskette, USB drive, Cloud storage location, etc. In yet other embodiments, the actual instructions are not present in the kit, but means for obtaining the instructions from a remote source, e.g., via the internet, are provided. An example of this embodiment is a kit that includes a web address where the instructions can be viewed and/or from which the instructions can be downloaded. As with the instructions, this means for obtaining the instructions is recorded on a suitable substrate.

The kit can further include any one or more of the following: a positive control sample, a negative control sample, a detectable binding agent for a marker specific for mononuclear inflammatory cells (MIC), e.g., CD3, CD5, CD4, CD7, CD8, CD20, and other markers of MIC, one or more reagents for performing an immunohistochemistry (IHC) staining reaction on a tumor tissue sample from a subject.

The various components of the kit may be present in separate containers or certain compatible components may be pre-combined into a single container, as desired.

EXAMPLES

Example 1

The main challenge around interpretation of tumor tissue stains for PD-L1 (e.g., TPS and MIDS scores, described in detail below) is to distinguish tumor from immune cells. This is especially true in gastric carcinoma since tumor and immune cells are of similar size and therefore very challenging to differentiate. Importantly, recent studies indicate that in certain tumor types expression of PD-L1 in immune as well as in tumor cells may be a good predictor of efficacy of anti-PD-1 immunotherapy (e.g., like pembrolizumab).

To address the challenges around companion diagnostic assay development timelines and scoring interpretation, we propose below a Combined Positive Score (CPS).

CPS for Use in Gastric Carcinoma
Samples Analyzed
Specimens from subjects having gastric carcinoma patients are analyzed. These samples can be from patients prior to treatment, during treatment, or after an initial round of treatment with a therapeutic agent, e.g., pembrolizumab.
Tissue Specimen Preparation and Staining
Specimens for analysis are formalin-fixed and paraffin-embedded (FFPE) tissue sections. Sections are cut to a desired thickness (e.g., 4 um thickness), placed on charged slides, and dried in an oven for one hour. For example, human tissue sections can be dried at 56-60° C. The cut sections can be stored in the dark at 2-8° C. and stained with the PD-L1 IHC assay within 6 months.

The IHC staining for PD-L1 expression is performed using the Dako Autostainer Link 48 platform (Dako AS480) and an automated staining protocol validated for the PD-L1 IHC 22C3 pharmDx assay. Deparaffinization, rehydration and target retrieval of the tissue sections is performed in the PT Link (Dako PT100) using a 3-in-1 procedure. Following incubation with the monoclonal mouse anti-human PD-L1 antibody (clone 22C3) or the Negative Control Reagent (NCR) (mouse IgG isotype control), specimens are incubated with anti-mouse linker antibody specific to the host species of the primary antibody, and then incubated with a ready-to-use visualization reagent consisting of secondary antibody molecules and horseradish peroxidase molecules coupled to a dextran polymer backbone. The enzymatic conversion of the subsequently added 3,3'-diaminobenzidine tetrahydrochloride (DAB) chromogen followed by DAB enhancer results in precipitation of a visible reaction product at the site of antigen. The specimens are then counterstained with Hematoxylin and coverslipped. Results are interpreted by direct observation using a light microscope. Assay performance is optimized for sensitivity with minimum non-specific staining by adjusting primary antibody concentration and reagent incubation times.

Staining Interpretation

Hematoxylin and Eosin stain (H&E) is used by the pathologist to confirm diagnosis and situate the tumor. Hematoxylin counterstain on the PD-L1 slide is used to estimate the number of cells. Tumor cells are typically larger than mononuclear inflammatory cells. Initially, PD-L1 expression is determined and interpreted as follows:

1. The Tumor Proportion Score (TPS): the percentage of tumor cells expressing PD-L1 on the cell membrane. Linear partial or complete cell membrane staining is interpreted as positive for PD-L1.

2. Mononuclear Inflammatory Density Score (MIDS): the ratio of the number of PD-L1 expressing mononuclear inflammatory cells infiltrating or adjacent to the tumor compared to the total number of tumor cells. The MIDS is recorded at a scale from 0 to 4 with (0=None; 1=Present, but less than one MIC for every 100 tumor cells (<1%; a negative result); 2=At least one MIC for every 100 tumor cells, but less than one MIC per 10 tumor cells (1-9%; a positive result); 3=At least one MIC for every 10 tumor cells, but fewer MIC's than tumor cells (10-99%; a positive result); 4=At least as many MIC's as tumor cells (≥100%; a positive result).

3. Combined Positive Score (CPS): the ratio of the number of PD-L1 positive tumor cells and PD-L1 positive mononuclear inflammatory cells (MIC) within the tumor nests and the adjacent supporting stroma (numerator) compared to the total number tumor cells (denominator; i.e., the number of PD-L1 positive and PD-L1 negative tumor cells). (See detailed description above for further details.) PD-L1 expression at any intensity is considered positive, i.e., weak (1+), moderate (2+), or strong (3+).

A cut-off is the score that differentiates diagnostically positive from diagnostically negative. The cut-off can be set to achieve the following goals:

1. Identify all responders (i.e., no false negatives); and
2. Minimize the number of non-responders (i.e., false positives).

It is expected that setting the cut-off at ≥1% for a positive result for the scores above, CPS will identify subjects who are responsive to anti-PD therapy that are missed by the TPS and MIDS analyses described above. The CPS scoring method is very reproducible between pathologists and therefore an excellent scoring algorithm to interpret PD-L1 expression to identify subjects eligible for anti-PD therapy.

CPS Used in Other Cancers

The CPS approach is generally applicable to any cancers expressing PD-L1 in either tumor and/or immune cells. For example, CPS can be used to analyze triple negative breast carcinoma using a similar cut-off value as described above.

Exemplary Embodiments

Non-limiting examples of embodiments of certain aspects of the subject disclosure are provided below.

1. A method for determining the eligibility of a subject having a malignancy for treatment with an anti-PD therapeutic agent, the method comprising: determining the number of viable PD-L1 positive tumor cells, the number of viable PD-L1 negative tumor cells, and the number of viable PD-L1 positive mononuclear inflammatory cells (MIC) in a tumor tissue sample from a subject having a malignancy; calculating a combined positive score (CPS) for the tumor tissue sample using the formula:

$$CPS = \frac{PD\text{-}L1 \text{ positive tumor cells} + PD\text{-}L1 \text{ positive } MIC}{PD\text{-}L1 \text{ positive tumor cells} + PD\text{-}L1 \text{ negative tumor cells}} \times 100\%$$

wherein the subject is eligible for treatment with an anti-PD therapeutic agent when the CPS is above a threshold.

2. The method of embodiment 1, wherein the threshold is from about 10% to about 1%.

3. The method of embodiment 1 or 2, wherein the threshold is 1%.

4. The method of any one of embodiments 1 to 3, wherein the tumor tissue sample is a tissue section of a tumor biopsy.

5. The method of embodiment 4, wherein PD-L1 is detected by immunohistochemistry (IHC) staining.

6. The method of embodiment 4 or 5, wherein the tumor tissue section is a formalin fixed and embedded in paraffin wax (FFPE) tumor tissue section.

7. The method of any one of embodiments 4 to 6, wherein the tissue section is stained.

8. The method of embodiment 7, wherein the stain is a hematoxylin and eosin (H&E) stain.

9. The method of any one of embodiments 4 to 8, wherein the viable PD-L1 positive tumor cells, the number of viable PD-L1 negative tumor cells, and the number of viable PD-L1 positive MIC are counted in the tumor nests and the adjacent supporting stroma of the tumor tissue sample.

10. The method of any one of embodiments 1 to 3, wherein the tumor tissue sample is a cell suspension.

11. The method of embodiment 10, wherein the number of viable PD-L1 positive tumor cells, the number of viable PD-L1 negative tumor cells, and the number of viable PD-L1 positive MIC in the tumor tissue sample are determining by flow cytometry.

12. The method of any one of embodiments 1 to 11, wherein one or more additional marker is detected in the tumor tissue sample.

13. The method of embodiment 12, wherein the marker is specific for MIC.

14. The method of embodiment 13, wherein the marker is selected from the group consisting of: CD3, CD5, CD4, CD7, CD8, and CD20.

15. The method of any one of embodiments 12 to 14, wherein PD-L1 and the one or more additional marker are detected simultaneously.

16. The method of any one of embodiments 12 to 14, wherein PD-L1 and the one or more additional marker are detected sequentially.

17. The method of any one of embodiments 1 to 16, wherein the method further comprises, prior to the determining step, contacting the tumor tissue sample with a detectable anti-PD-L1 binding agent.

18. The method of embodiment 17, wherein the detectable anti-PD-L1 binding agent comprises an anti-PD-L1 antibody or binding fragment thereof.

19. The method of any one of embodiments 1 to 3, wherein the number of viable PD-L1 positive tumor cells, the number of viable PD-L1 negative tumor cells, and the number of viable PD-L1 positive MIC in the tumor tissue sample are determined by single cell sequencing.

20. The method of any preceding embodiment, wherein the malignancy is selected from the group consisting of: gastric cancer, head and neck cancer, renal cell carcinoma, urothelial/bladder carcinoma, ovarian carcinoma, myeloma, melanoma, lung cancer, squamous cell carcinoma, classical Hodgkin's lymphoma, and breast cancer (e.g., triple negative breast cancer, hormone receptor positive (ER and/or PR) and Her2 positive breast cancer), small cell lung cancer, salivary gland carcinoma, vulvar carcinoma, thyroid carcinoma, anal canal carcinoma, biliary carcinoma, mesothelioma, cervical carcinoma, and neuroendocrine carcinoma.

21. The method of embodiment 18, wherein the malignancy is gastric cancer.

22. The method of embodiment 18, wherein the malignancy is head and neck cancer.

23. The method of embodiment 18, wherein the head and neck cancer is head and neck squamous cell carcinoma (HNSCC).

24. The method of any preceding embodiment, wherein the anti-PD therapeutic agent inhibits the anti-cell death activity of PD-1/PD-L1.

25. The method of any preceding embodiment, wherein the anti-PD therapeutic agent comprises an anti-PD or anti-PD-L1 specific antibody or binding fragment thereof.

26. The method of embodiment 25, wherein the anti-PD therapeutic agent is selected from the group consisting of: Avelumab (MSB0010178C), Nivolumab, Pembrolizumab, BMS-936559, MPDL3280A, Pidilizumab, and MEDI4736.

27. The method of embodiment 23, wherein the anti-PD therapeutic agent is Avelumab.

28. The method of any preceding embodiment, wherein the subject is a human.

29. A kit for determining the eligibility of a subject having a malignancy for treatment with an anti-PD therapeutic agent, comprising: a detectable PD-L1 specific binding agent; and instructions for calculating a combined positive score (CPS).

30. The kit of embodiment 29, further comprising a positive and negative control sample.

31. The kit of embodiment 29 or 30, further comprising a detectable binding agent for a marker specific for mononuclear inflammatory cells (MIC).

32. The kit of embodiment 31, wherein the marker specific for MIC is selected from the group consisting of: CD3, CD5, CD4, CD7, CD8, and CD20.

33. The kit of any one of embodiments 29 to 32, further comprising one or more reagents for performing an immunohistochemistry (IHC) staining reaction on a tumor tissue sample from a subject.

A method of treatment is provided. In some embodiments, the method comprises:

determining the number of viable PD-L1 positive tumor cells, the number of viable PD-L1 negative tumor cells, and the number of viable PD-L1 positive mononuclear inflammatory cells (MIC) in a tumor tissue sample from a subject having a malignancy; calculating a combined positive score (CPS) for the tumor tissue sample using the formula:

$$CPS = \frac{PD\text{-}L1 \text{ positive tumor cells} + PD\text{-}L1 \text{ positive } MIC}{PD\text{-}L1 \text{ positive tumor cells} + PD\text{-}L1 \text{ negative tumor cells}} \times 100\%$$

and treating the subject with an anti-PD therapeutic agent if the CPS is above a threshold.

It will also be recognized by those skilled in the art that, while the invention has been described above in terms of preferred embodiments, it is not limited thereto. Various features and aspects of the above described invention may be used individually or jointly. Further, although the invention has been described in the context of its implementation in a particular environment, and for particular applications those skilled in the art will recognize that its usefulness is not limited thereto and that the present invention can be beneficially utilized in any number of environments and implementations. Accordingly, the claims set forth below should be construed in view of the full breadth and spirit of the invention as disclosed herein.

What is claimed is:

1. A method for determining the eligibility of a subject having a malignancy for treatment with an anti-PD therapeutic agent, the method comprising: determining the number of viable PD-L1 positive tumor cells, the number of viable PD-L1 negative tumor cells, and the number of viable PD-L1 positive mononuclear inflammatory cells (MIC) in a tumor tissue sample from a subject having a malignancy; and calculating a combined positive score (CPS) for the tumor tissue sample using the formula:

$$CPS = \frac{PD\text{-}L1 \text{ positive tumor cells} + PD\text{-}L1 \text{ positive } MIC}{\text{total number of viable tumor cells}} \times 100\%$$

wherein the subject is eligible for treatment with said anti-PD therapeutic agent when the CPS is above a threshold from 60 to 1.

2. The method of claim 1, wherein the threshold is 1.

3. The method of claim 1, wherein the tumor tissue sample is a tissue section of a tumor biopsy.

4. The method of claim 3, wherein PD-L1 is detected by immunohistochemistry (IHC) staining.

5. The method of claim 3, wherein the tumor tissue section is a formalin fixed and embedded in paraffin wax (FFPE) tumor tissue section.

6. The method of claim 3, wherein the tissue section is stained.

7. The method of claim 3, further comprising staining a section from the biopsy with a hematoxylin and eosin (H&E) stain.

8. The method of claim 3, wherein the viable PD-L1 positive tumor cells, the total number of viable tumor cells, and the number of viable PD-L1 positive MIC are counted in the tumor nests and the adjacent supporting stroma of the tumor tissue sample.

9. The method of claim 1 wherein the number of PD-L1 positive tumor cells and the number of PD-L1 positive MIC are determined using an anti-PD-L1 antibody or a PD-L1 binding fragment thereof.

10. The method of claim 1, wherein the malignancy is selected from the group consisting of: gastric cancer, head and neck cancer, renal cell carcinoma, urothelial/bladder carcinoma, ovarian carcinoma, myeloma, melanoma, lung cancer, squamous cell carcinoma, classical Hodgkin's lymphoma, breast cancer, triple negative breast cancer, hormone receptor positive (ER and/or PR) and Her2 positive breast cancer, small cell lung cancer, salivary gland carcinoma, vulvar carcinoma, thyroid carcinoma, anal canal carcinoma, biliary carcinoma, mesothelioma, cervical carcinoma, and neuroendocrine carcinoma.

11. The method of claim 1, wherein the anti-PD therapeutic agent is selected from the group consisting of: Avelumab, Nivolumab, Pembrolizumab, BMS-936559, MPDL3280A, Pidilizumab, and MEDI4736.

12. The method of claim 1 further comprising administering the anti-PD therapeutic agent to the subject when the CPS is above the threshold.

13. The method of claim 1, wherein the anti-PD therapeutic agent is Pembrolizumab.

14. The method of claim 13, wherein the malignancy is non-small cell lung carcinoma.

15. The method of claim 1, further comprising administering Pembrolizumab to the subject when the CPS is above the threshold.

16. The method of claim 13, wherein the malignancy is esophageal carcinoma.

17. The method of claim 1, wherein the threshold is 10.

18. The method of claim 13 wherein the malignancy is gastric carcinoma.

19. The method of claim 13 wherein the malignancy is cervical carcinoma.

20. The method of claim 13 wherein the malignancy is urothelial carcinoma.

21. The method of claim 13 wherein the malignancy is head and neck carcinoma.

22. The method of claim 1, wherein the threshold is 20.

* * * * *